United States Patent
Ambrozinski et al.

(10) Patent No.: US 11,413,007 B2
(45) Date of Patent: Aug. 16, 2022

(54) NON-CONTACT ACOUSTIC RADIATION FORCE BASED (ARF-BASED) GENERATION OF BROAD BANDWIDTH MECHANICAL WAVES USING AIR-COUPLED ULTRASOUND

(71) Applicant: University of Washington, Seattle, WA (US)

(72) Inventors: Lukasz Ambrozinski, Seattle, WA (US); Matthew O'Donnell, Seattle, WA (US); Ivan Pelivanov, Seattle, WA (US); Soon Joon Yoon, Seattle, WA (US); David Li, Seattle, WA (US); Shaozhen Song, Seattle, WA (US); Ruikang K. Wang, Bellevue, WA (US); Tueng T. Shen, Redmond, WA (US); Liang Gao, Seattle, WA (US)

(73) Assignee: University of Washington, Seattle, WA (US)

( * ) Notice: Subject to any disclaimer, the term of this patent is extended or adjusted under 35 U.S.C. 154(b) by 934 days.

(21) Appl. No.: 16/304,054

(22) PCT Filed: May 26, 2017

(86) PCT No.: PCT/US2017/034801
§ 371 (c)(1),
(2) Date: Nov. 21, 2018

(87) PCT Pub. No.: WO2017/205809
PCT Pub. Date: Nov. 30, 2017

(65) Prior Publication Data
US 2020/0315570 A1     Oct. 8, 2020

Related U.S. Application Data

(60) Provisional application No. 62/413,563, filed on Oct. 27, 2016, provisional application No. 62/341,775, filed on May 26, 2016.

(51) Int. Cl.
    *A61B 8/14*        (2006.01)
    *A61B 8/10*        (2006.01)
    (Continued)

(52) U.S. Cl.
    CPC ............... *A61B 8/10* (2013.01); *A61B 3/102* (2013.01); *A61B 3/16* (2013.01); *A61B 8/0858* (2013.01);
    (Continued)

(58) Field of Classification Search
    CPC ......... A61B 3/102; A61B 3/16; A61B 5/0051; A61B 5/0066; A61B 5/442; A61B 8/0858;
    (Continued)

(56) References Cited

U.S. PATENT DOCUMENTS

| | | | |
|---|---|---|---|
| 5,636,635 A | 6/1997 | Massie et al. | |
| 5,824,908 A | 10/1998 | Schindel et al. | |

(Continued)

FOREIGN PATENT DOCUMENTS

| | | |
|---|---|---|
| CN | 104434028 | 3/2015 |
| WO | 2013106385 | 6/2015 |

(Continued)

OTHER PUBLICATIONS

Ambrozinski et al., "Acoustic Micro-Tapping For Non-Contact 4D Imaging of Tissue Elasticity", Scientific Reports, vol. 6, Article No. 38967, Dec. 23, 2016.

(Continued)

*Primary Examiner* — Mark D Remaly
(74) *Attorney, Agent, or Firm* — Kilpatrick Townsend & Stockton LLP

(57) ABSTRACT

Methods and systems for measuring one or more properties of a soft material employ air transmitted ultrasound that is reflected from the soft material to generate a mechanical (Continued)

wave in the soft material. A method of measuring one or more properties of a soft material includes transmitting ultrasound through air to an interface boundary between the soft material and air. Force is applied to the soft material by reflecting the ultrasound from the soft material. A mechanical wave is generated in the soft material as a result of the force applied to the soft material. Propagation of the mechanical wave in the soft material is measured with an imaging system. One or more properties of the soft material is determined based on the measured propagation of the mechanical wave in the soft material.

24 Claims, 15 Drawing Sheets

(51) Int. Cl.
A61B 3/10 (2006.01)
A61B 3/16 (2006.01)
A61B 8/08 (2006.01)
A61B 8/00 (2006.01)

(52) U.S. Cl.
CPC .......... *A61B 8/4444* (2013.01); *A61B 8/4488* (2013.01); *A61B 8/485* (2013.01)

(58) Field of Classification Search
CPC ....... A61B 8/10; A61B 8/4444; A61B 8/4488; A61B 8/485; G01N 2291/02475; G01N 29/0654; G01N 29/221; G01N 29/2456; G01N 29/26; G10K 11/26
See application file for complete search history.

(56) References Cited

U.S. PATENT DOCUMENTS

| | | |
|---|---|---|
| 7,999,945 B2 | 8/2011 | Zara |
| 2008/0228073 A1 | 9/2008 | Silverman et al. |
| 2013/0218012 A1 | 8/2013 | Specht et al. |
| 2014/0323862 A1 | 10/2014 | Silverman et al. |
| 2015/0005632 A1 | 1/2015 | Sakaguchi |
| 2015/0148655 A1 | 5/2015 | Haupt et al. |
| 2015/0351722 A1 | 12/2015 | Chen et al. |
| 2016/0015365 A1 | 1/2016 | Li |
| 2016/0128558 A1 | 5/2016 | Larin et al. |
| 2016/0174834 A1 | 6/2016 | Eslami et al. |
| 2016/0192835 A1 | 7/2016 | Matz et al. |
| 2016/0242650 A1 | 8/2016 | Chen et al. |
| 2017/0107558 A1 | 4/2017 | Chen et al. |

FOREIGN PATENT DOCUMENTS

| | | |
|---|---|---|
| WO | 2016077173 | 5/2016 |
| WO | 2017205809 | 11/2017 |

OTHER PUBLICATIONS

Ambrozinski et al., "Application of Air-Coupled Ultrasonic Transducers for Damage Assessment of Composite Panels", 6th European Workshop on Structural Health Monitoring, Jan. 2012 , pp. 122-129.
Ambrozinski et al., "Air-Coupled Acoustic Radiation Force for Non-Contact Generation of Broadband Mechanical Waves in Soft Media," Applied Physics Letters, vol. 109, 043701, Jul. 25, 2016.
Ampo, et al., "Leveling Viscous Fluids Using Ultrasonic Waves," Japanese Journal of Applied Physics, vol. 43, No. 5B, pp. 2857-2861, May 28, 2004.
Azar, et al., 2-D High-Frame-Rate Dynamic Elastography Using Delay Compensated and Angularly Compounded Motion Vectors: Preliminary Results, IEEE, vol. 57, No. 11, Nov. 2010.
Bercoff et al., "Sonic Boom in Soft Materials: The Elastic Cerenkov Effect", Applied Physics Letters, vol. 84, No. 12, Apr. 2004, pp. 2202-2204.
Bercoff et al., "Study of Viscous and Elastic Properties of Soft Tissues Using Supersonic Shear Imaging", IEEE Symposium on Ultrasonics, Oct. 2003, pp. 925-928.
Bercoff et al., "Supersonic Shear Imaging: A New Technique For Soft Tissue Elasticity Mapping", IEEE Transactions on Ultrasonics, Ferroelectrics, and Frequency Control, vol. 51, No. 4, Aug. 9, 2004, pp. 396-409.
Boote et al., "Lamellar Orientation in Human Cornea in Relation to Mechanical Properties", J Struct Biol., vol. 149, No. 1, Jan. 2005, pp. 1-6.
Doherty et al., "Acoustic Radiation Force Elasticity Imaging in Diagnostic Ultrasound", IEEE Trans Ultrason Ferroelectr Freq Control., vol. 60, No. 4, Apr. 2013, pp. 685-701.
Dupps, et al., "Corneal Strain Mapping by Optical Coherence Elastography," Invest. Ophthalmos Via Science, vol. 48, No. 13, 2007, Abstract Only.
Elsheikh et al., "Biomechanical Properties of Human and Porcine Corneas," ScienceDirect, pp. 783-790, 2008.
Elsheikh et al., "Mechanical Anisotropy of Porcine Cornea and Correlation with Stromal Microstructure", Experimental Eye Research, vol. 88, No. 6, Jun. 2009, pp. 1084-1091.
Eskandari, et al., "Bandpass Sampling of High-Frequency Tissue Motion," IEEE, vol. 58, No. 7, Jul. 2011.
Fatemi et al., "Vibro-Acoustography: An Imaging Modality Based on Ultrasound-Stimulated Acoustic Emission", Proc. Natl. Acad. Sci. U. S. A., vol. 96, No. 12, Jun. 8, 1999, pp. 6603-6608.
Ford, et. al., "Method for Optical Coherence Elastography of the Cornea," J. of Biomed. Optics, 016005-1-7, vol. 16, No. 1, Jan. 2011.
Fowlkes et al., "American Institute of Ultrasound in Medicine Consensus Report on Potential Bioeffects of Diagnostic Ultrasound", Executive Summary, Journal of Ultrasound in Medicine, vol. 27, No. 4, Apr. 2008, pp. 503-515.
Gan et al., "High-Resolution, Air-Coupled Ultrasonic Imaging of Thin Materials", IEEE Transactions on Ultrasonics, Ferroelectrics, and Frequency Control, vol. 50, No. 11, Dec. 8, 2003, pp. 1516-1524.
Gennisson et al., "Ultrasound Elastography: Principles and Techniques", Diagn Interv Imaging, vol. 94, No. 5, May 2013, pp. 487-495.
Gomez Alvarez-Arenas , "Acoustic Impedance Matching of Piezoelectric Transducers to the Air", IEEE Transactions on Ultrasonics, Ferroelectrics, and Frequency Control, vol. 51, No. 5, Aug. 9, 2004, pp. 624-633.
Gomez Alvarez-Arenas et al., "Passive Focusing Techniques For Piezoelectric Air-Coupled Ultrasonic Transducers", Ultrasonics, vol. 67, Apr. 2016, pp. 85-93.
Grandia et al., "NDE Applications of Air-Coupled Ultrasonic Transducers", Proceedings of IEEE Ultrasonics Symposium, Nov. 7-10, 1995, pp. 697-709.
Guan, et al., "Quantitative Evaluation of Degenerated Tendon Model Using Combined Optical Coherence Elastography and Acoustic Radiation Force Method," J. of Biomed. Optics., vol. 18, No. 11, Nov. 2013.
Han et al., "Air Puff Induced Corneal Vibrations: Theoretical Simulations and Clinical Observations", Journal of Refractive Surgery, vol. 30, No. 3, Mar. 2014, pp. 208-213.
Han et al., "Quantitative Assessment of Corneal Viscoelasticity Using Optical Coherence Elastography and a Modified Rayleigh-Lamb Equation", J Biomed Opt., vol. 20, No. 2, Feb. 2015, pp. 020501-1-020501-3.
Holland et al., "Air-Coupled, Focused Ultrasonic Dispersion Spectrum Reconstruction in Plates", The Journal of the Acoustical Society of America, vol. 115, No. 6, Jun. 3, 2004, pp. 2866-2872.
Hwang, et al., "Non-Contact Acoustic Radiation Force Impulse Microscopy Via Photoacoustic Detection for Probing Breast Cancer Cell Mechanics," Biomedical Optics Express, vol. 6, No. 1, Dec. 3, 2014.
Ingard et al., "Acoustic Fountain Effect", Journal of Acoustical Society of America, vol. 48, No. 114, 1970.

(56) References Cited

OTHER PUBLICATIONS

Johnson, et al., "Role of Corneal Elasticity in Damping of Intraocular Pressure," Investigative Ophthalmology & Visual Science, vol. 48, No. 6, Jun. 2007.
Karabutov et al., "Relaxation Dynamics of a Broadband Nanosecond Acoustic Pulse in a Bubbly Medium", Acoustical Physics, vol. 52, No. 5, Sep. 2006, pp. 582-588.
Kasai et al., "Real-Time Two-Dimensional Blood Flow Imaging Using an Autocorrelation Technique", IEEE Transactions on Sonics and Ultrasonics, vol. 32, No. 3, Mar. 1985, pp. 458-464.
Kazys et al., "Air-Coupled Ultrasonic Investigation of Multi-Layered Composite Materials", Ultrasonics, vol. 44, Dec. 22, 2006, pp. e819-e822.
Kennedy et al., "In Vivo Dynamic Optical Coherence Elastography Using a Ring Actuator", Opt Express., vol. 17, No. 24, Nov. 2009, pp. 21762-21772.
Kim et al., "Narrow Band Photoacoustic Lamb Wave Generation for Nondestructive Testing Using Candle Soot Nanoparticle Patches," Appl. Phys. Letter 115, 102902 (2019), Sep. 3, 2019.
Kling, et al., "Corneal Biomechanical Changes After Collagen Cross-Linking from Porcine Eye Inflation Experiments," Investigative Ophthalmology & Visual Science, vol. 51, No. 8, Aug. 2010.
Li et al., "Determining Elastic Properties of Skin by Measuring Surface Waves From an Impulse Mechanical Stimulus Using Phase-Sensitive Optical Coherence Tomography", Journal of the Royal Society Interface, vol. 9, No. 70, May 7, 2012, pp. 831-841.
Li et al., "Noncontact All-Optical Measurement of Corneal Elasticity", Optics Letters, vol. 37, No. 10, May 15, 2012, pp. 1625-1627.
Li et al., "Revealing Anisotropic Properties of Cornea at Different Intraocular Pressures Using Optical Coherence Elastography", Proceedings of SPIE 9710, Optical Elastography and Tissue Biomechanics III, Mar. 2016.
Li, et al., "Differentiating Untreated and Cross-Linked Porcine Corneas of the Same Measured Stiffness with Optical Coherence Elastography," Journal of Biomedical Optics, vol. 19, No. 11, Nov. 2014.
Liang et al., "Acoustomotive Optical Coherence Elastography for Measuring Material Mechanical Properties", Opt Lett., vol. 34, No. 19, Oct. 2009, pp. 2894-2896.
Liu et al., "Evaluation of corneal thickness and topography in normal eyes using the Orbscan corneal topography system", British journal of ophthalmology, vol. 83, 1999, pp. 774-778.
Loupas et al., "An Axial Velocity Estimator For Ultrasound Blood Flow Imaging, Based on a Full Evaluation of the Doppler Equation by Means of a Two-Dimensional Autocorrelation Approach", IEEE Transactions on Ultrasonics, Ferroelectrics, and Frequency Control, vol. 42, No. 4, Jul. 1995, pp. 672-688.
Lubinski et al., "Speckle Tracking Methods For Ultrasonic Elasticity Imaging Using Short-Time Correlation", IEEE Transactions on Ultrasonics, Ferroelectrics, and Frequency Control, vol. 46, No. 1, Jan. 1999, pp. 82-96.
Manapuram et al., "Estimation of Shear Wave Velocity in Gelatin Phantoms Utilizing PhS-SSOCT", Laser Physics, vol. 22, No. 9, Sep. 2012, pp. 1439-1444.
Manduca et al., "Magnetic Resonance Elastography: Non-Invasive Mapping of Tissue Elasticity", Med. Image Anal., vol. 5, No. 4, Dec. 2001, pp. 237-254.
Medeiros, et al., "Evaluation of the Influence of Corneal Biomechanical Properties on the Intraocular Pressure Measurements Using the Ocular Response Analyzer," J. Glaucoma, pp. 364-370, vol. 15, No. 5, Oct. 2006.
Muthupillai et al., "Magnetic Resonance Elastography", Nature Medicine, vol. 2, No. 5, May 1, 1996, pp. 601-603.
Muthupillai et al., "Magnetic Resonance Elastography by Direct Visualization of Propagating Acoustic Strain Waves", Science, vol. 269, No. 5232, Sep. 29, 1995, pp. 1854-1857.
Nguyen et al., "Assessment of Viscous and Elastic Properties of Sub-Wavelength Layered Soft Tissues Using Shear Wave Spectroscopy: Theoretical Framework and In Vitro Experimental Validation", IEEE Trans Ultrason Ferroelectr Freq Control, vol. 58, No. 11, Nov. 2011, pp. 2305-2315.
Nguyen et al., "In Vivo Evidence of Porcine Cornea Anisotropy Using Supersonic Shear Wave Imaging", Investigative Ophthalmology & Visual Science, vol. 55, No. 11, Oct. 2014, pp. 7545-7552.
Nguyen et al., "Shear Wave Elastography Using Amplitude-Modulated Acoustic Radiation Force and Phase-Sensitive Optical Coherence Tomography", J Biomed Opt., vol. 20, No. 1, Jan. 2015, pp. 016001-1-016001-7.
Nguyen et al., "Visualizing Ultrasonically-Induced Shear Wave Propagation Using Phase-Sensitive Optical Coherence Tomography For Dynamic Elastography", Opt Lett., vol. 39, No. 4, Feb. 2014, pp. 838-841.
Nightingale et al., "A Finite Element Model of Remote Palpation of Breast Lesions Using Radiation Force: Factors Affecting Tissue Displacement", Ultrasonic Imaging, vol. 22, No. 1, Jan. 2000, pp. 35-54.
Nightingale et al., "On the Feasibility of Remote Palpation Using Acoustic Radiation Force", J. Acoust. Soc. Am., vol. 110, No. 1, Jul. 2001, pp. 625-634.
O'Donnell et al., "Internal Displacement and Strain Imaging Using Ultrasonic Speckle Tracking", IEEE Transactions on Ultrasonics, Ferroelectrics and Frequency Control, vol. 41, No. 3, Jan. 1, 1994, pp. 314-325.
Ophir et al., "Elastography: A Quantitative Method for Imaging the Elasticity of Biological Tissues", Ultrasonic Imaging, vol. 13, No. 2, Apr. 1991, pp. 111-134.
Palmeri et al., "A Finite-Element Method Model of Soft Tissue Response to Impulsive Acoustic Radiation Force", IEEE Transactions on Ultrasonics, Ferroelectrics, and Frequency Control, vol. 52, No. 10, Dec. 19, 2005, pp. 1699-1712.
Palmeri et al., "Quantifying Hepatic Shear Modulus in Vivo Using Acoustic Radiation Force", Ultrasound in Medicine & Biology, vol. 34, No. 4, 2008, pp. 546-558.
Pelivanov et al., "A New Fiber-Optic Non-Contact Compact Laser-Ultrasound Scanner for Fast Non-Destructive Testing and Evaluation of Aircraft Composites", J Appl Phys., vol. 115, No. 11, Mar. 21, 2014, pp. 113105-1-113105-11.
Qi et al., "Phase-Resolved Acoustic Radiation Force Optical Coherence Elastography", J Biomed Opt., vol. 17, No. 11, Nov. 2012, pp. 110505-1-110505-3.
Razani et al., "Feasibility of Optical Coherence Elastography Measurements of Shear Wave Propagation in Homogeneous Tissue Equivalent Phantoms", Biomed Opt Express., vol. 3, No. 5, May 1, 2012, pp. 972-980.
Sandrin et al., "Shear Modulus Imaging with 2-D Transient Elastography", IEEE Transactions on Ultrasonics, Ferroelectrics, and Frequency Control, vol. 49, No. 4, Apr. 2002, pp. 426-435.
Sarvazyan et al., "Biomedical Applications of Radiation Force of Ultrasound: Historical Roots and Physical Basis", Ultrasound Med Biol., vol. 36, No. 9, Sep. 2010, pp. 1379-1394.
Sarvazyan et al., "Shear Wave Elasticity Imaging: A New Ultrasonic Technology of Medical Diagnostics", Ultrasound Med. Biol., vol. 24 No. 9, Nov. 1998, pp. 1419-1435.
Schindel et al., "Focusing of Ultrasonic Waves in Air Using a Micro Machined Fresnel Zone-Plate", Ultrasonics, vol. 35, No. 4, Jun. 1997, pp. 275-285.
Schmitt, "OCT Elastography: Imaging Microscopic Deformation and Strain of Tissue", Optics Express, vol. 3, No. 6, Sep. 14, 1998, pp. 199-211.
Simon et al., "Ultrasonic Atomization of Liquids in Drop-Chain Acoustic Fountains", Journal of Fluid Mechanics, vol. 766, Mar. 2015, pp. 129-146.
Singh et al., "Phase-Sensitive Optical Coherence Elastography at 1.5 Million A-Lines Per Second", Opt Lett., vol. 40, No. 11, Jun. 1, 2015, pp. 2588-2591.
Singh, et al., "Three-Dimensional Mapping of Corneal Elasticity Using Optical Coherence Elastography," SPIE, 2015.
Song et al., "Comb-push Ultrasound Shear Elastography (CUSE): A Novel Method for Two-dimensional Shear Elasticity Imaging of Soft Tissues", IEEE Transactions on Medical Imaging, vol. 31, No. 9, Sep. 2012, pp. 1821-1832.

(56) References Cited

OTHER PUBLICATIONS

Song et al., "Shear Modulus Imaging by Direct Visualization of Propagating Shear Waves with Phase-Sensitive Optical Coherence Tomography", Journal of Biomedical Optics, vol. 18, No. 12, Dec. 2013, pp. 121509-1-121509-7.

Song et al., "Strategies to Improve Phase-Stability of Ultrafast Swept Source Optical Coherence Tomography For Single Shot Imaging of Transient Mechanical Waves at 16 KHz Frame Rate", Appl Phys Lett., vol. 108, No. 19, May 9, 2016, pp. 191104-1-191104-5.

Song et al., "Tracking Mechanical Wave Propagation Within Tissue Using Phase-Sensitive Optical Coherence Tomography: Motion Artifact and its Compensation", Journal of Biomedical Optics, vol. 18, No. 12, Dec. 2013.

Tanter et al., "Quantitative Assessment of Breast Lesion Viscoelasticity: Initial Clinical Results Using Supersonic Shear Imaging", Ultrasound in Medicine & Biology, vol. 34, No. 9, Sep. 2008, pp. 1373-1386.

Torr, "The Acoustic Radiation Force", American Journal of Physics, vol. 52, No. 2, 1984, pp. 402-408.

Vappou et al., "Quantitative Viscoelastic Parameters Measured by Harmonic Motion Imaging," IPEM, May 19, 2009.

Wang et al., "Noncontact Measurement of Elasticity For the Detection of Soft-Tissue Tumors Using Phase-Sensitive Optical Coherence Tomography Combined With a Focused Air-Puff System", Opt Lett., vol. 37, No. 24, Dec. 15, 2012, pp. 5184-5186.

Wang et al., "Shear Wave Imaging Optical Coherence Tomography (SWI-OCT) for Ocular Tissue Biomechanics", Opt Lett., vol. 39, No. 1, Jan. 1, 2014, pp. 41-44.

Wang et al., "Tissue Doppler Optical Coherence Elastography for Real Time Strain Rate and Strain Mapping of Soft Tissue", Applied Physics Letters, vol. 89, No. 144103, Oct. 4, 2006, 3 pages.

Wang, et al., "Optical Coherence Elastography for Tissue Characterization: A Review," J Biophotonics, pp. 279-302, Apr. 2015.

Wang, A Focused Air-Pulse System for Optical-Coherence-Tomography-Based Measurements of Tissue Elasticity, Laser Physics Letters, 10, 2013.

Wang, et al., "Noncontact Depth-Resolved Micro-Scale Optical Coherence Elastography of the Cornea," Biomed Optics Express, vol. 5, No. 11, Oct. 6, 2014.

Welter et al., "Focusing of Longitudinal Ultrasonic Waves in Air With an Aperiodic Flat Lens", Journal of the Acoustical Society of America, vol. 130, No. 5, Nov. 2011, pp. 2789-2796.

Wieser et al., "Multi-Megahertz OCT: High quality 3D Imaging at 20 Million A-Scans and 4.5 GVoxels Per Second", Opt Express, vol. 18, No. 14, Jul. 5, 2010, pp. 14685-14704.

Wollensak, et al., "Stress-Strain Measurements of Human and Porcine Corneas After Riboflavin-Ultraviolet-A-Induced Cross-Linking," Laboratory Science, Mar. 17, 2003.

Wood et al., "The Physical and Biological Effects of High-frequency Sound-waves of Great Intensity", Philosophical Magazine, vol. 4, No. 22, 1927, pp. 417-436.

Fincke et al., "Non-Contact Laser Ultrasound (NCLUS) for Medical Imaging and Diagnosis", Available Online at:-https://clrccires.colorado.edu/presentations/R/R10.pdf, Jun. 30, 2016, 18 pages.

PCT/US2017/034801 , "International Search Report and Written Opinion", dated Aug. 16, 2017, 8 pages.

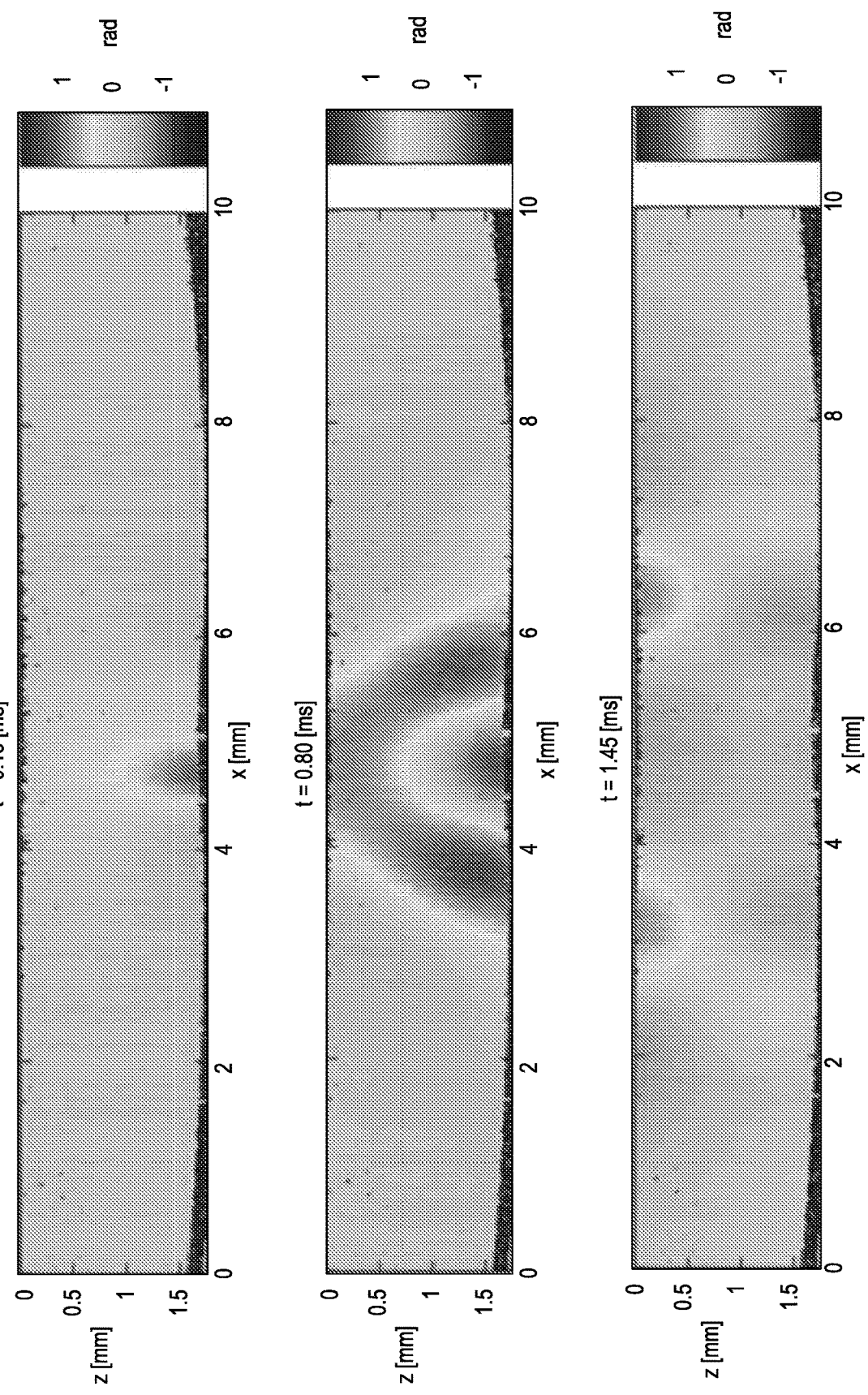

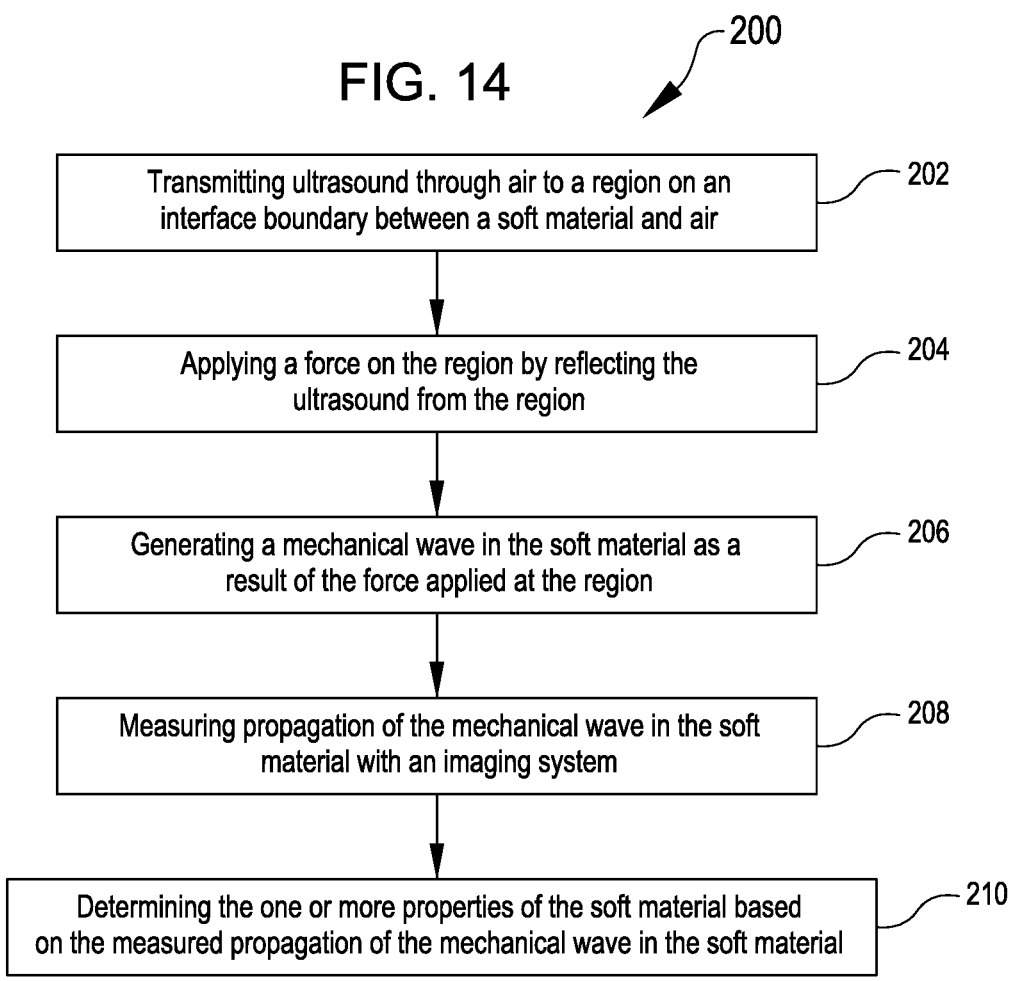

NON-CONTACT ACOUSTIC RADIATION FORCE BASED (ARF-BASED) GENERATION OF BROAD BANDWIDTH MECHANICAL WAVES USING AIR-COUPLED ULTRASOUND

CROSS-REFERENCES TO RELATED APPLICATIONS

The present application is a U.S. 371 of International Application No. PCT/US2017/034801, filed May 26, 2017, which claims the benefit of U.S. Provisional Application No. 62/341,775, filed May 26, 2016 and U.S. Provisional Application No. 62/413,563, filed Oct. 27, 2016, the entire contents of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. R01EY026532, awarded by the National Institutes of Health. The government has certain rights in the invention.

BACKGROUND

The stiffness of a soft tissue can be clinically valuable information with respect to diagnosis of disease, especially when combined with conventional medical imaging. Elastography is the term applied to the mapping of the elastic properties of a soft tissue. Different elastography techniques have been developed based on magnetic resonance imaging (MRI) and ultrasound (US) modalities.

Dynamic elastography techniques derive the elastic properties of a soft tissue from the speed of a propagating wave launched within tissue. Optical coherence tomography (OCT) has recently been used in dynamic elastography studies to measure the speed of the propagating wave. High spatial resolution and high sensitivity make OCT an excellent modality to measure the speed of a propagating wave in a soft tissue.

For clinical applications of dynamic elastography, a totally non-contact system for generation/detection of a mechanical wave is desirable, especially for application to soft tissues such as the eye. Existing non-contact systems for generation/detection of a mechanical wave in a soft tissue, however, may fail to measure elastic properties of the soft tissue sufficiently for diagnostic purposes. Accordingly, new and/or improved systems and methods for mapping elastic properties of a soft tissue remain of interest.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Methods and systems for measuring one or more elastic properties of a soft material generate a mechanical wave in the soft material by applying an acoustic radiation force to the soft material. The acoustic radiation force is applied by reflecting ultrasound from a region on an interface boundary between the soft material and air. The ultrasound is transmitted through air to the region, thereby generating the mechanical wave in the soft material without directly contacting the soft material. The methods and systems are suitable for use in many applications in which a non-contact dynamic elastography approach is desirable, such as application to a patient's cornea. In many embodiments, the region has an elongated shape so that the resulting propagating wave approximates a plane wave, thereby simplifying subsequent determination of the one or more elastic properties from the observed propagation of the mechanical wave.

Thus, in one aspect, a method of measuring one or more properties of a soft material is provided. The method includes transmitting ultrasound through air to a region on an interface boundary between the soft material and air. The ultrasound reflects from the region, thereby applying a force on the region. A mechanical wave is generated in the soft material as a result of the force applied at the region. Propagation of the mechanical wave in the soft material is measured with an imaging system. The one or more properties of the soft material is determined based on the measured propagation of the mechanical wave in the soft material.

The method of measuring one or more properties of a soft material can employ ultrasound having any suitable frequency. For example, the ultrasound can have a frequency equal to or greater than 20 kHz.

In many embodiments of the method of measuring one or more properties of a soft material, the region has an elongated shape configured to generate a plane wave or a near plane wave in the soft material. For example, the region can have an elongated shape having a width and a length that is at least ten times the width.

Any suitable approach can be used to transmit the ultrasound through air to the region. For example, transmitting the ultrasound through air to the region can include focusing the ultrasound onto the region using at least one of a focused ultrasonic transducer, an acoustic lens, an acoustic mask, a focusing mirror, and a Fresnel plate. Transmitting the ultrasound through air to the region can include directing the ultrasound to an acoustic mask disposed adjacent to the interface boundary. The acoustic mask can have an elongated aperture. A length of the elongated aperture can be at least ten times a width of the elongated aperture. Transmitting the ultrasound through air to the region can include transmitting the ultrasound by an array of ultrasonic transducers. Transmitting the ultrasound through air to the region can include transmitting the ultrasound by an ultrasound transducer coupled to the air.

In many embodiments of the method of measuring one or more properties of a soft material, measuring the propagation of the mechanical wave in the soft material with the imaging system includes generating a time sequence of images of the mechanical wave. The imaging system can include at least one of an optical imaging system, an ultrasound imaging system, and magnetic resonance imaging ("MRI") system. Determining the one or more properties of the soft material based on the measured propagation of the mechanical wave in the soft material can include generating a spatial map of elastic modulus of the soft material for locations in the soft material based on measured displacements of the locations in the soft material in the time sequence of images.

In many embodiments of the method of measuring one or more properties of a soft material, the imaging system includes an optical coherence tomography ("OCT") system. For example, the system can include a phase-sensitive OCT system. A phase of the OCT signal at a pixel in an image of the time sequence of images can be used to detect displacement of a location in the soft material corresponding to the pixel. In many embodiments, the time sequence of images includes both two-dimensional and three-dimensional OCT images that are used to measure displacements at locations in the soft material induced by the mechanical wave.

The method of measuring one or more properties of a soft material can be employed with any suitable soft material. For example, the soft material can be one of a cornea, skin, a biopsy sample, and a gel-based material.

The method of measuring one or more properties of a soft material can be employed to measure intraocular pressure of an eye. For example, the soft material can include an eye having a cornea. The focal region can be on an interface boundary between the cornea and air. The mechanical wave can be generated in the cornea. And the one or more properties of the soft material can include an intraocular pressure of the eye.

In another aspect, a system for measuring one or more properties of a soft material is described. The system includes an ultrasound transducer assembly, an imaging system, a processor, and a tangible memory device. The ultrasound transducer assembly is operable to transmit ultrasound through air to a region on an interface boundary between the soft material and the air. The ultrasound reflects from the region thereby applying a force on the region. The application of the force to the region generates a mechanical wave in the soft material. The imaging system is configured to generate image data of propagation of the mechanical wave in the soft material. The tangible memory device stores non-transitory instructions executable by the processor to cause the processor to process the image data generated by the imaging system to determine one or more properties of the soft material.

The system for measuring one or more properties of a soft material can employ ultrasound having any suitable frequency. For example, the ultrasound can have a frequency equal to or greater than 20 kHz.

In many embodiments of the system for measuring one or more properties of a soft material, the region has an elongated shape configured to generate a plane wave or a near plane wave in the soft material. For example, the region can have an elongated shape having a width and a length that is at least ten times the width.

The system can include any suitable components for transmitting the ultrasound through air to the region. For example, the ultrasound transducer assembly can include at least one of a focused ultrasonic transducer, an acoustic lens, an acoustic mask, a focusing mirror, and a Fresnel plate. The ultrasound transducer assembly can include an acoustic mask configured to be disposed adjacent to the interface boundary. The acoustic mask can have an elongated aperture. For example, a length of the elongated aperture can be at least ten times a width of the elongated aperture. The ultrasound transducer assembly can include an array of ultrasonic transducers. In many embodiments, the ultrasound transducer assembly includes an ultrasound transducer coupled to air.

In many embodiments of the system for measuring one or more properties of a soft material, the image data generated by the imaging system includes a time sequence of images of the mechanical wave. The imaging system can include at least one of an optical imaging system, an ultrasound imaging system, and magnetic resonance imaging ("MRI") system. The tangible memory device can store non-transitory instructions executable by the processor to cause the processor to generate a spatial map of elastic modulus of the soft material for locations in the soft material based on measured displacements of the locations in the soft material in the time sequence of images.

In many embodiments of the system for measuring one or more properties of a soft material, the imaging system includes an optical coherence tomography ("OCT") system. For example, the imaging system can include a phase-sensitive OCT system. A phase of the OCT signal at a pixel in an image of the time sequence of images can be used to detect displacement of a location in the soft material corresponding to the pixel. In many embodiments of the system for measuring one or more properties of a soft material, the time sequence of images includes both two-dimensional and three-dimensional OCT images that are used to measure displacements at locations in the soft material induced by the mechanical wave.

The system for measuring one or more properties of a soft material can be employed with any suitable soft material. For example, the soft material can be one of a cornea, skin, a biopsy sample, and a gel-based material.

The system for measuring one or more properties of a soft material can be employed to measure intraocular pressure of an eye. For example, the soft material can include an eye having a cornea. The focal region can be on an interface boundary between the cornea and air. The mechanical wave can be generated in the cornea. And the one or more properties of the soft material can include an intraocular pressure of the eye.

For a fuller understanding of the nature and advantages of the present invention, reference should be made to the ensuing detailed description and accompanying drawings.

BRIEF DESCRIPTION OF THE DRAWINGS

FIG. 14 is a simplified schematic diagram of acts of a method of measuring one or more properties of a soft material using air-transmitted ultrasound to generate a mechanical wave in the soft material, in accordance with embodiments.

DETAILED DESCRIPTION

Figure 1:
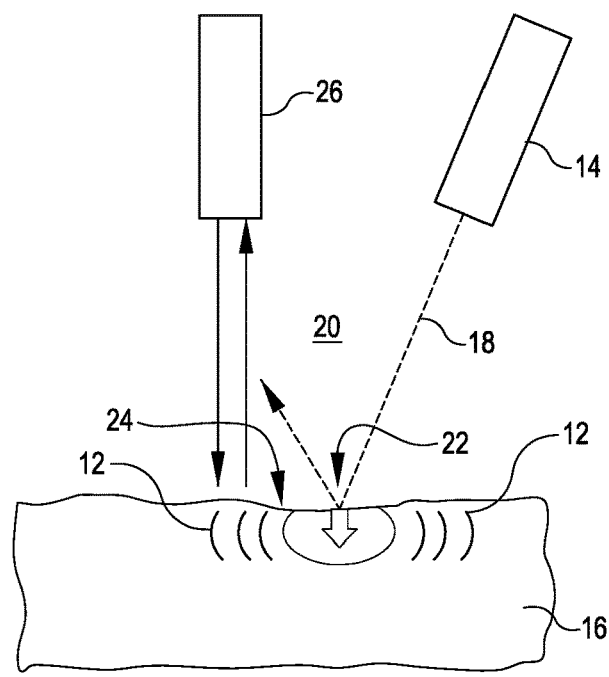
FIG. 1 is a simplified schematic diagram illustrating a dynamic elastography technique in which a mechanical wave is generated in a soft material by reflecting air-transmitted ultrasound from the soft material at a region on an interface between the soft material and air, in accordance with embodiments.

In the following description, various embodiments of the present invention will be described. For purposes of explanation, specific configurations and details are set forth in order to provide a thorough understanding of the embodiments. It will, however, also be apparent to one skilled in the art that the present invention may be practiced without the specific details. Furthermore, well-known features may be omitted or simplified in order not to obscure the embodiment being described.

Methods and systems are described herein for dynamic elastography using non-contact mechanical stimulation of a soft material (i.e., a material having an elastic modulus in a range of 1 Pa to 1 MPa) via the application of an air-coupled ultrasound pulse to induce significant transient mechanical displacement at the boundary of a soft material using reflection-based radiation force. The induced transient mechanical displacement generates a mechanical wave that propagate through the soft material. The propagation of the mechanical wave is measured with an imaging system and the resulting measurement used to determine elastic properties of the soft material. In many embodiments, the imaging system includes an optical coherence tomography (OCT) system configured to perform high-speed phase-sensitive optical coherence tomography. The imaging protocol can be configured to perform two- (repeated A-scan, i.e. depth scan, at one spatial location, representing one space dimension plus time), three- (repeated B-scan, i.e. cross-sectional scan, representing two space dimensions plus time), and/or four- (repeated C-scan, i.e. three space dimensions plus time) scans. Methods and systems described herein provide for high-resolution and quantitative dynamic elastography of a soft material (e.g., any suitable soft material including any suitable soft tissue) at near real-time imaging rates.

While certain embodiments described herein employ an OCT system to track displacements of locations within the soft material generated by the mechanical wave, other suitable imaging systems can also be used. Other suitable imaging systems that can be used to track displacements within the soft material include ultrasound (US) and magnetic resonance imaging (MRI) imaging systems. The tracked displacements can be processed to generate maps of the elastic modulus of the soft material using existing approaches.

Methods and systems are described herein for non-contact dynamic elastography are believed to be especially well suited for applications in which direct contact with the soft material under study is not desired and may actually be prohibited. In contrast, nearly all prior art methods for elastography employ direct contact with the soft material under study. For many applications in biomedicine and other fields, however, a totally non-contact system (for both excitation and detection of a mechanical wave in the soft material) is desirable and, in some cases, required. In particular, for dynamic elastography to be used routinely in ophthalmology and dermatology, and potentially for biopsy characterization, a robust non-contact technology for generating the mechanical wave is preferred.

Methods and systems are described herein for non-contact dynamic elastography of a soft material employ an air-coupled US beam pulse that is reflected from a region on an interface surface between the soft material and air. As described herein, the air-coupled US beam pulse can be reflected from the air/soft-material interface so as to generate significant transient shear displacement through reflection-based acoustic radiation force (ARF). Unlike relatively inefficient ARF techniques using acoustic loss and scattering mechanisms, the reflection based approach described herein can be used to efficiently convert acoustic energy into transient shear displacement in the target soft material. Systems described herein include an OCT imaging system and an air-coupled focused US transducer and are referred to herein as optical coherence elastography (OCE) systems. A fully non-contact, non-invasive and clinically translatable OCE system is described herein that is configured to quantitatively map elasticity of a soft material at high spatial resolution. As discussed herein, the performance of an OCE system was demonstrated via ex-vivo measurements on a porcine cornea.

As described herein, non-contact mechanical excitation of the soft material can be performed with a specially designed piezoelectric transducer that transmits an US beam pulse through air. The US beam pulse is directed onto the region on the air/soft-material interface. Reflection of the US beam pulse from the air/soft-material interface applies significant transient compressive ARF to the soft material at the region. The applied transient compressive ARF induces a transient displacement at that surface (including a shear one), which generates a propagating mechanical wave in the lateral (transverse to the surface normal) direction. The reflection of the US beam pulse from the focal region is analogous to a hammer tapping wood or a stick beating a drum where a localized, transient force on the target creates significant transient localized deformation of the soft material. Due to the large difference in acoustic impedances of air and the soft material, the efficiency of the conversion of the acoustic energy in the US beam pulse to the energy transferred to the mechanical wave approaches one hundred percent. In many applications, the transient displacement of the soft material need only be about one μm and the acoustic pressure only a few kPa, a level far below any potential damage thresholds for soft tissue and, thus, absolutely non-invasive. Generation of the mechanical wave via reflection of the US beam pulse from the focal region is referred to herein as acoustic micro-tapping (AμT).

Previous ARF methods in elastography use loss and scattering mechanisms to convert acoustic energy into displacements. In contrast, embodiments for dynamic elastography described herein use reflection-based radiation force for highly efficient displacement generation. In reflection mode, the radiation pressure P (force per unit area) is given by equation (1), where R is the reflection coefficient at the air/soft-material interface, I is the acoustic intensity (watts/m$^2$) and c is the sound speed.

$$P=(1+R^2)I/c \quad (1)$$

For air-coupled ultrasound, the reflection coefficient at the air-tissue boundary is nearly 1 so that the radiation force can be approximated as P=2I/c. Since the sound speed in air is low (about 340 m/sec) and all acoustic intensity is converted into radiation pressure, significant force can be produced at modest acoustic pressures.

High frequency ultrasound is absorbed strongly by air. Air-coupled ultrasound, however, can be delivered at modest pressures from suitable distances for practical applications, as described herein. By shaping the high-frequency ultrasound field using a suitable approach (e.g., via a focused transducer, with acoustic masks and lenses, via a phased transducer array) the radiation pattern (i.e., spatial distribution of I) can be configured to efficiently excite a high bandwidth (i.e., short wavelength) mechanical wave suitable for high spatial resolution mapping of elastic properties.

Air-coupled US (i.e. sound with frequencies >20 kHz) is well known in non-destructive testing (NDT) of solids in which it is used mostly for generation of guided and Lamb modes in plates. The conversion is performed at the air/plate interface by Snell-Descartes law when the wave vector of the generated wave in the plate has to be aligned along the surface of the plate. Thus, the induced waves in the plate maintain the carrier frequency of the pump US wave.

Acoustic radiation force is not related to the carrier waveform, but to the intensity, spatial shape of the pump beam, and duration of the ultrasound pulse. For pulsed insonification, the ARF acts like a "hammer" on the surface. Relaxation of the displacement induced by this "hammer" generates the mechanical wave.

ARF has been used previously to induce a mechanical wave in soft tissue by absorption of the focused pump US beam in a desired region. In such previous applications of ARF, however, the pump US beam is propagated through a coupling material, not through air. Accordingly, applicants believe that using radiation force by reflection (not absorption) of the pump beam (propagating in air) at the air/medium interface to produce surface transient displacements using sound frequencies in the ultrasound range (i.e. >20 kHz and up to several MHz) to generate a propagating mechanical wave in soft tissues has not been previously demonstrated.

Methods and systems described herein for non-contact dynamic elastography of a soft material may not be as generally applicable as conventional radiation force methods utilizing coupling materials because the mechanical wave is generated at the surface in embodiments described herein, not within the volume. There are, however, a large number of physical and medical problems where the methods and systems for non-contact dynamic elastography described herein can be applied, such as, for example, measuring one or more elastic properties of an eye, skin, blood vessels and intestinal channels, etc.

In some embodiments, the pump US beam is focused to the air/soft-material interface from the air side to optimize spatial resolution of the mechanical wave imaging by maximizing the bandwidth of generated mechanical wave and increasing conversion efficiency. Any suitable approach can be used to direct the pump US beam to a region on the air/soft material interface. For example, suitable approaches for directing the pump US beam to the region are believed to include focused air-coupled transducers, lenses, zone plates, and suitably shaped reflecting mirrors.

Referring now to the drawings, in which like reference numerals represent like parts throughout the several views, FIG. 1 illustrates the general concept of acoustic radiation force based (ARF-based) generation of a broad bandwidth mechanical wave 12 using air-coupled ultrasound. An air-coupled transducer 14 is located in a suitable position and orientation relative to a soft material 16 under study. The air-coupled transducer 14 delivers an US pulse 18 through air 20 to a region 22 on the air/soft material interface 24. Reflection of the US pulse 18 from the soft material 16 at the region 22 applies transient compressive acoustic radiation force(s) to the soft material 16 at the region 22. The application of the transient compressive ARF(s) to the soft material 16 at the region 22 generates a transient local displacement(s) of the soft material 16 at the region 22. Relaxation of the transient local displacement(s) generates the mechanical wave 12 (e.g., a shear/guided/interface/Lamb waves) that propagate through the soft material 16. The elastic properties of the soft material 16 can be assessed by detecting the mechanical wave 12 (on either side or both sides of the region 22) using a detector of mechanical waves 26 (e.g., a suitable imaging system or other suitable means). Because the transient induced displacement(s) of the soft material 16 is localized to the region 22, and the soft material 16 has a non-zero viscosity, a broad-band mechanical wave 12 is generated in the lateral direction. The bandwidth of the mechanical wave 12 is determined by the configuration of the region 22 and the temporal characteristics of the US pulse 18. The detector of mechanical waves 26 can include a suitable imaging system and can be located in the air adjacent to the soft material 16.

Figure 2:
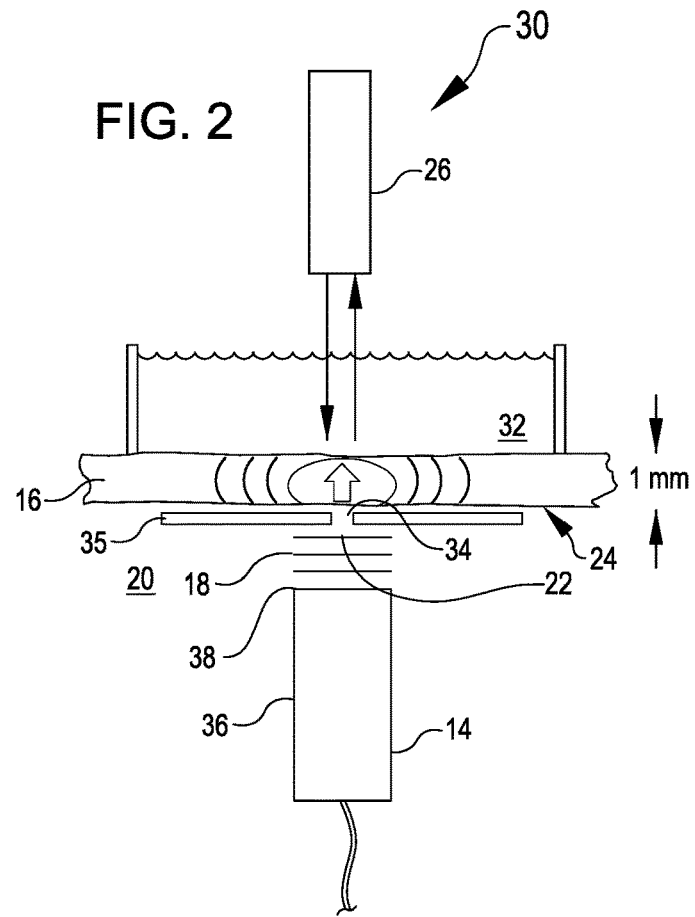
FIG. 2 is a simplified schematic diagram illustrating the use of a diaphragm having an elongated opening to transmit air-transmitted ultrasound to a region on a tissue-mimicking gelatin phantom, in accordance with embodiments.

FIG. 2 illustrates an experimental setup 30 that was used to demonstrate dynamic elastography using an AμT generated mechanical wave as described herein. A tissue mimicking phantom (soft material 16) was made of 8% w/w gelatin (Sigma-Aldrich, G2500) and with 0.02% w/w titanium dioxide (TiO2) added as optical scatters for OCT imaging. The thickness of the phantom is 1.6 mm. A 5 mm water layer 32 was placed above the gelatin phantom 16 to mimic mechanical loading of the soft material 16 similar to that for the cornea at the front of the eye. A 1 MHz air-coupled ultrasound transducer 14 was used to transmit an US pulse beam 18 to the underside of a tissue-equivalent gelatin phantom 16 through a narrow slit 34 (0.34 mm by 15 mm long) in a diaphragm 36 to shape the region 22 on the soft material 16. Detection of the generated mechanical wave 12 was performed from the opposite side of the phantom with a PhS-OCT system 26 as described in Song S, Huang Z, Nguyen T-M, Wong E Y, Arnal B, O'Donnell M, Wang R K, Shear modulus imaging by direct visualization of propagating shear waves with phase-sensitive optical coherence tomography Journal of Biomedical Optics 2013; 18(12): 121509-1-7, the full disclosure of which is incorporated herein by reference.

In the experimental setup 30, the 1 MHz air-coupled ultrasound transducer 14 was constructed and included a PZT-based transducer 36 with a matching layer 38 (a 0.45 μm pore size nylon membrane filter, Cat. No. 7404-004, "GE Healthcare UK Limited", Little Chalfont, UK) bounded to the surface of the transducer 36 with a silicon adhesive. The matching layer 38 was used to enhance coupling of the US pulse 18 into the air 20. The resonance frequency of the PZT-based transducer 36 is 1 MHz and the emitting aperture is 12.2 mm in diameter. The transducer 14 was located 1 cm away from the soft material 16 surface beneath the bottom surface of the phantom 16. The transducer 14 was excited using a burst signal with repetition frequency of 20 Hz. The burst signal was a linear chirp 400V in peak to peak amplitude with a duration of 400 μs. The linear chirp was used to minimize potential standing wave effects between the transducer 14 and the phantom surface 24. The bandwidth of the driving voltage signal ranged from 0.9 MHz to 1.1 MHz (i.e. chirp has a time-bandwidth product of approximately 80).

In the experimental setup 30, the pressure amplitude in the generated US beam 18 was measured with a 28 μm PVDF transducer calibrated in the frequency band 50 kHz-30 MHz. The measured acoustic pressure amplitude in the generated US beam 18 was about 1 kPa at 1 cm from the air-coupled transducer surface.

In the experimental setup 30, the diaphragm 36 having the narrow slit 34 was made from two glass cover plates (170 um thick) separated by 0.34 mm one from another and placed in the air 20 0.5 mm below the phantom surface 24 to localize the ARF-based excitation. Note that the slit 34 was used to mimic a focused US beam, which can be obtained in many different suitable ways (e.g., using a focused air-coupled transducer, lensing, zone plates and properly shaped reflective mirrors). The width of the slit 34 was chosen to be close to the US wavelength in air, which is the typical diffraction limit for shaping. As a result, the US beam 18 interacted with the soft material 16 at a strip of the phantom surface 24 about 12 mm long by 0.34 mm wide. The size of the strip was selected to maximize the bandwidth of the generated mechanical wave 12. The strip excitation was used instead of a round spot to induce directional (i.e., one dimensional) mechanical wave propagation, minimize diffraction loss, and approximate a one-dimensional propagation model.

In the experimental setup 30, the PhS-OCT system 26 was used to detect the guided mechanical wave 12 generated in the gelatin phantom 16 from the opposite side of the phantom 16. The PhS-OCT system 26 operated in MB-mode (i.e., repeated B-scan over time) at a 91.2 kHz A-scan rate, enabling mechanical wave tracking in time and space frame by frame.

The phase difference in PhS-OCT is linearly proportional to displacement, measured to be more than 1 um in the excitation point, which can be easily detected with, for example, OCT. An at least 40 dB signal-to-noise ratio (SNR) was achieved using the experimental setup 30, thereby demonstrating suitability of the dynamic elastography approach described herein, under conditions similar to those for real biomedical measurements, for real biomedical applications with high SNR.

Figure 3:
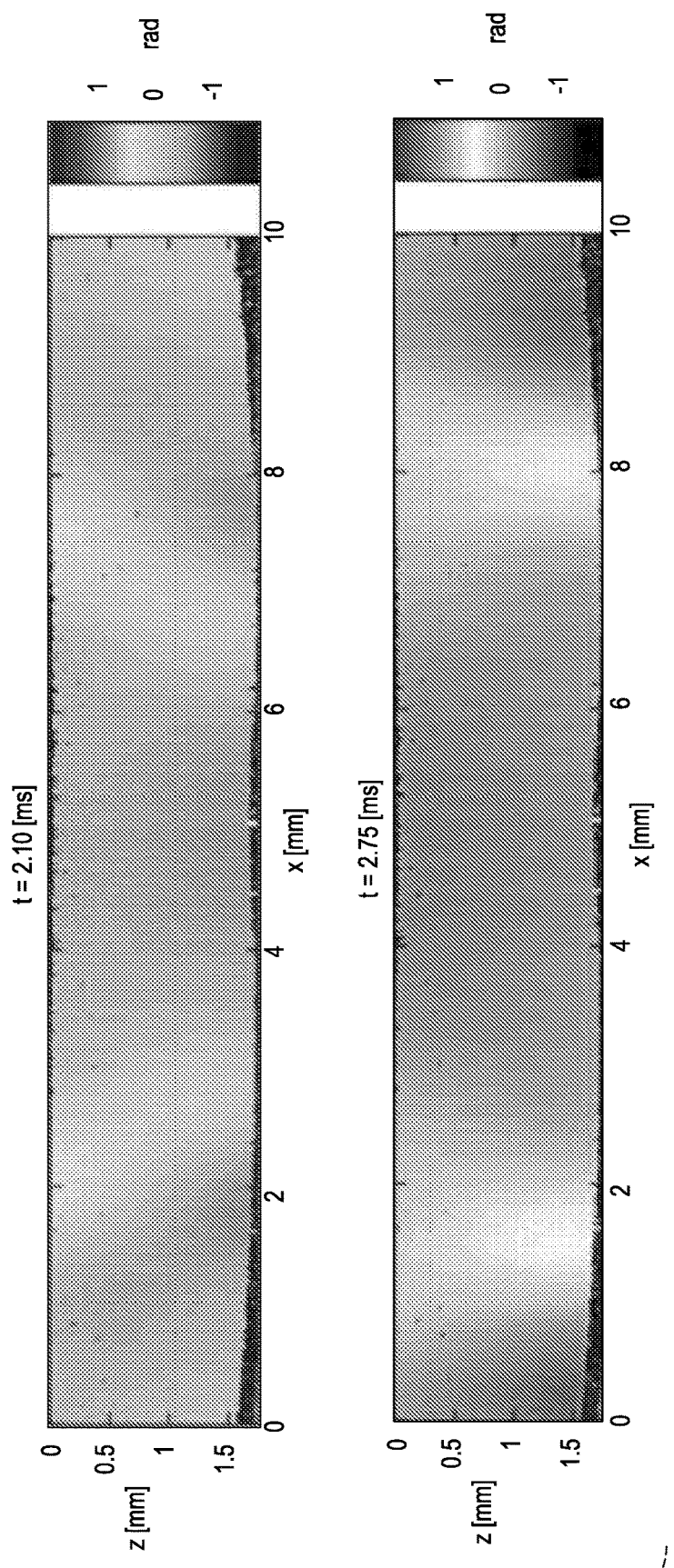
FIG. 3 shows a time sequence of images of a propagating wave in the gelatin phantom of FIG. 2.

Five sequential instants stepped by 0.65 ms in propagation of the mechanical wave 12 recorded with OCT are shown in FIG. 3. In the near field from the source, the wave 12 shows its divergence in both X and Z directions until the wave 12 reaches the interface of the gelatin phantom with water. Beyond that instant, the wave 12 is guided in the X (lateral) direction with opposite phases at the interfaces with water (Z=0) and air (Z=1.6 mm).

Figure 4A:
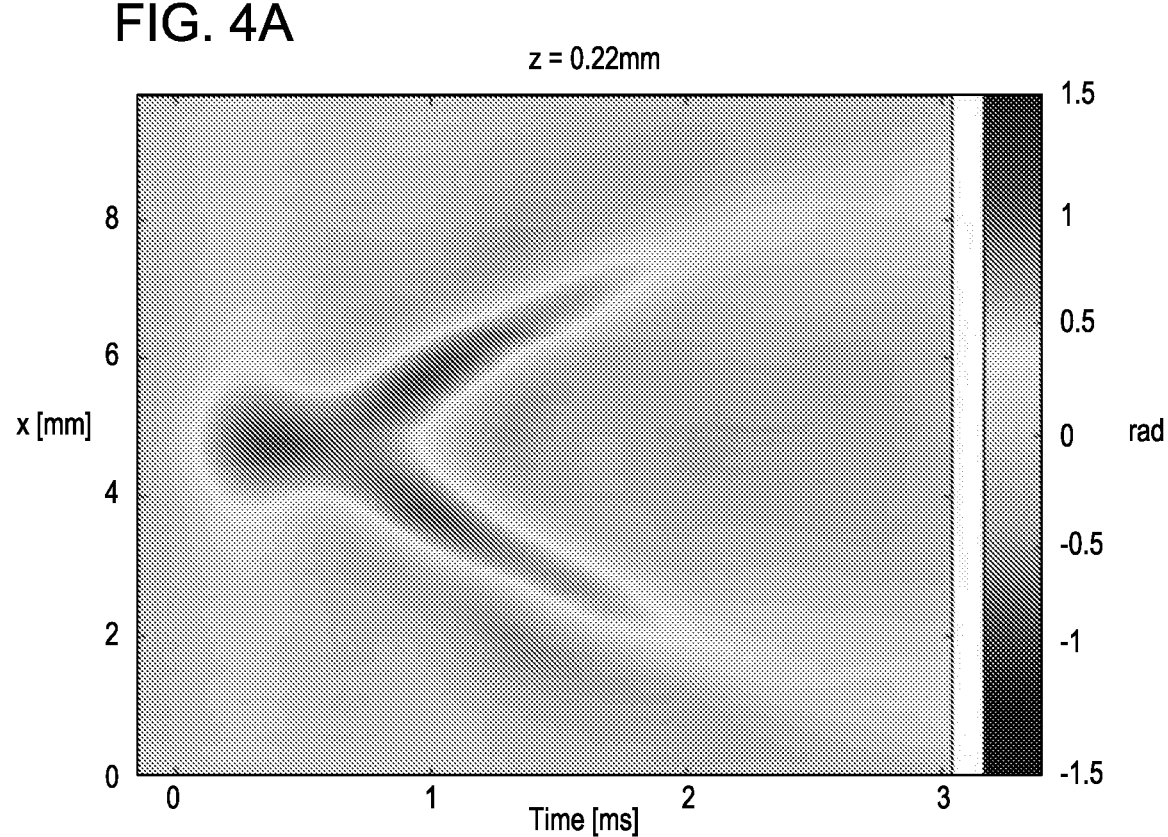
FIGS. 4A, 4B, and 4C show two dimensional maps of temporal profiles for a mechanical wave propagating in the gelatin phantom of FIG. 2.
Figure 4B:
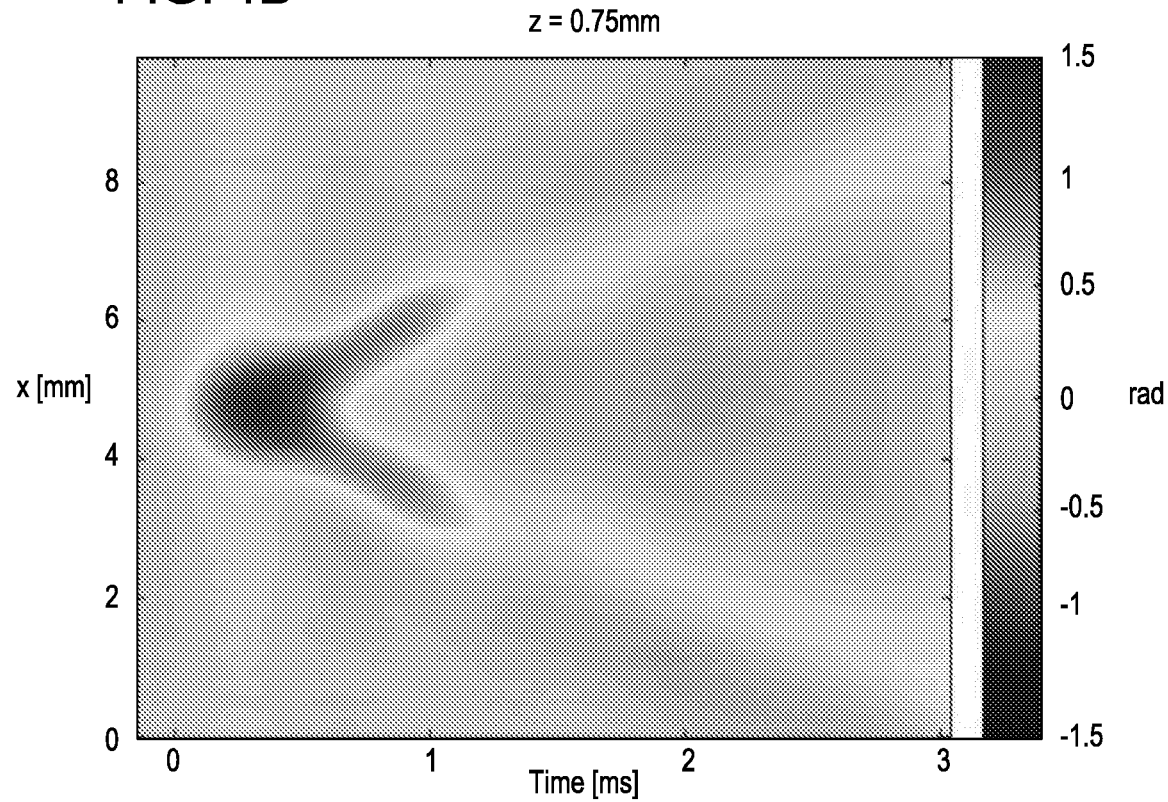
Figure 4C:
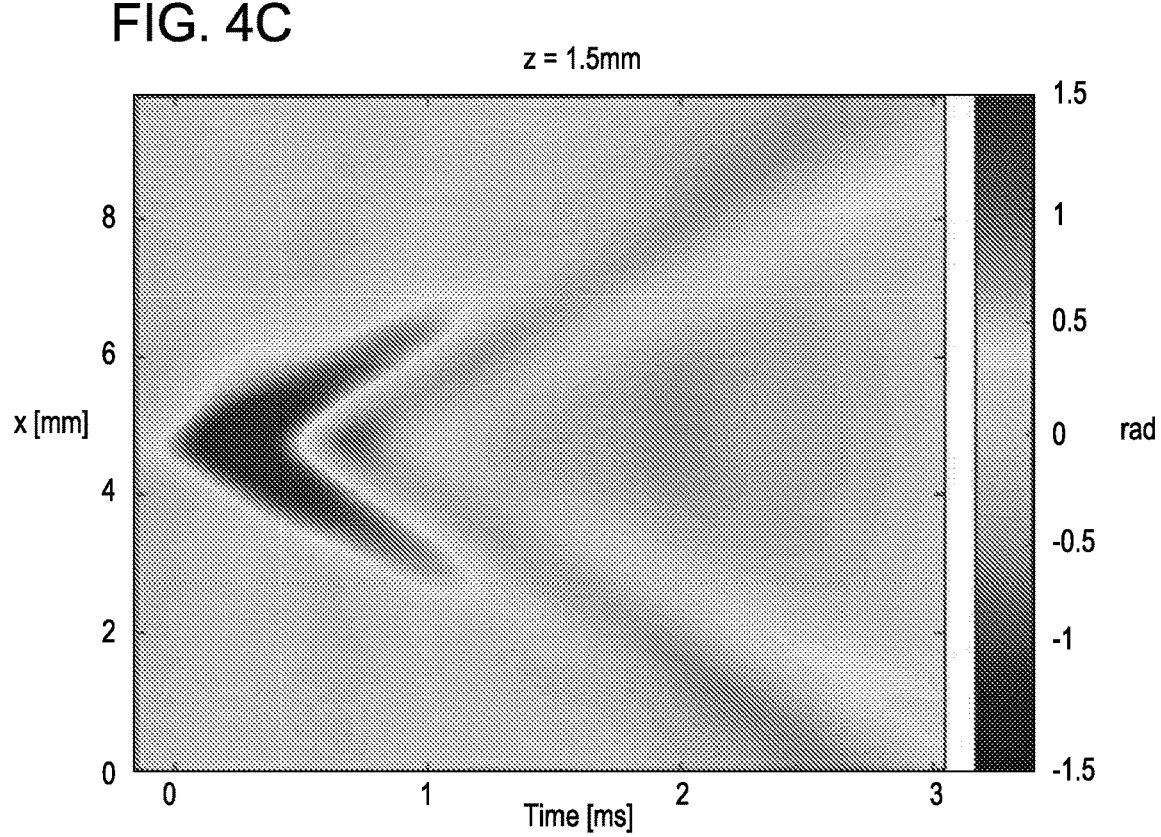

FIG. 4A through FIG. 4C shows how the temporal shape of the mechanical wave 12 changes during propagation from the center of the excitation to the side in the X (lateral) direction for three different Z (in depth) positions: close to the water interface (FIG. 4A), the phantom center (FIG. 4B), and air interface (FIG. 4C). It can be seen that the waveform is not conserved even in the near field and even when the line source was used for excitation, i.e. wave propagation is strongly dispersive. The dispersion is depth dependent, showing the opposite sign in displacement at water and air interfaces at the same time instant.

Using known techniques, the speed of the mechanical wave 12 at suitable points within the soft material 16 can be determined. The determined speeds of the wave 12 within the soft material 16 can be used to map elasticity of the soft material 16. The speed of the wave 12, however, depends on frequency, as can be seen from FIG. 4A through FIG. 4C. The speed of the wave 12 also depends on excitation geometry and the type of the generated mode. In the experimental setup 30, the 1.6 mm thick gelatin phantom 16 with a water layer 32 on one side was used to mimic an eye cornea. The phantom 16 has two different interfaces and, therefore, the generated mode of the wave 12 is not purely shear and, moreover, is not purely symmetric or asymmetric. Thus, mechanical wave dispersion cannot be ignored in most real situations, and tissue elasticity μ of a cornea may not be determinable with a simple mechanical relationship given in equation (2) (where V is the speed of mechanical wave).

$$\mu = \rho V^2 \qquad (2)$$

To determine the tissue elasticity μ of a cornea, the solution of an eigenvalue problem may need to be considered, which, in general, can be a serious mathematical problem. For one-dimensional propagation of a broad bandwidth mechanical wave, however, the determination of the tissue elasticity μ of a cornea is greatly simplified and the solution can be found numerically using known techniques. For example, the mechanical wave dispersion curve determined experimentally can be fit with that found theoretically to determine tissue elasticity of a cornea, using techniques described in Han Z, Aglyamov S, LI J, Wang S, Vantipalli S, Wu C, Liu C-H, Twa M D, Larin K V. Quantitative assessment of corneal viscoelasticity using optical coherence elastography and a modifies Rayleigh-Lamb equation. J. Biomed. Opt. 2015; 20(2):020501, the full disclosure of which is incorporated herein by reference. Accordingly, the dynamic elastography using AμT based wave generation described herein can be used for soft tissue elasticity mapping of a cornea, as well as other suitable soft materials.

For applications in ophthalmology and dermatology, sub-mm resolution elasticity maps are believed to be suitable. To produce sub-mm resolution elasticity maps, the transient displacement scale, or the wavelength of the excited mechanical wave, should be less than one mm. Consequently, the spatial extent and bandwidth of the mechanical excitation should be sub-mm and multi-kHz, respectively. As described herein, a novel focused air-coupled piezoelectric transducer was designed, built, and demonstrated that can efficiently transfer a 1 MHz US pulse through air to the air/soft-material interface with sufficient acoustic energy to launch a mechanical wave having a few kHz bandwidth with μm-scale displacements that can be easily detected/imaged/measured by a high frame rate OCT system. It is believed by the applicants that this is the first demonstration of efficient excitation of a high bandwidth mechanical wave in a soft material with air-coupled AμT. Details of the transducer design, including spatial, temporal, and amplitude characteristics, are described herein.

For clinical application of non-contact AμT-OCE, a suitable phase-shift optical coherence tomography (PhS-OCT) system can be used to track a high bandwidth mechanical wave propagating in four dimensions (i.e., three space dimensions plus time—4D). Embodiments described herein include a 16 kHz frame rate PhS-OCT imaging system that was developed and is suitable for three-dimensional (3D) imaging (i.e., 4D data acquisition) over large dimensions. The 16 kHz frame rate PhS-OCT imaging system was used to capture mechanical wave propagation over a soft-material volume in a fraction of a second (over 3 Hz volume rate) to reconstruct a 3D elasticity map from a single AμT excitation per plane within the soft-material volume. A more detailed description of the 16 kHz frame rate PhS-OCT imaging system is provided herein.

Combining AμT for non-contact transient wave excitation with 4-D PhS-OCT imaging of the propagating mechanical wave yields a single-sided, non-contact method to non-invasively measure the elasticity of soft materials such as biological tissue. As described herein, system performance was demonstrated on a porcine cornea with 4D displacement maps and 3D wave speed reconstructions based on the 4D displacement maps. It is believed by applicants that the resulting images presented herein are the first images of their kind.

Figure 5:
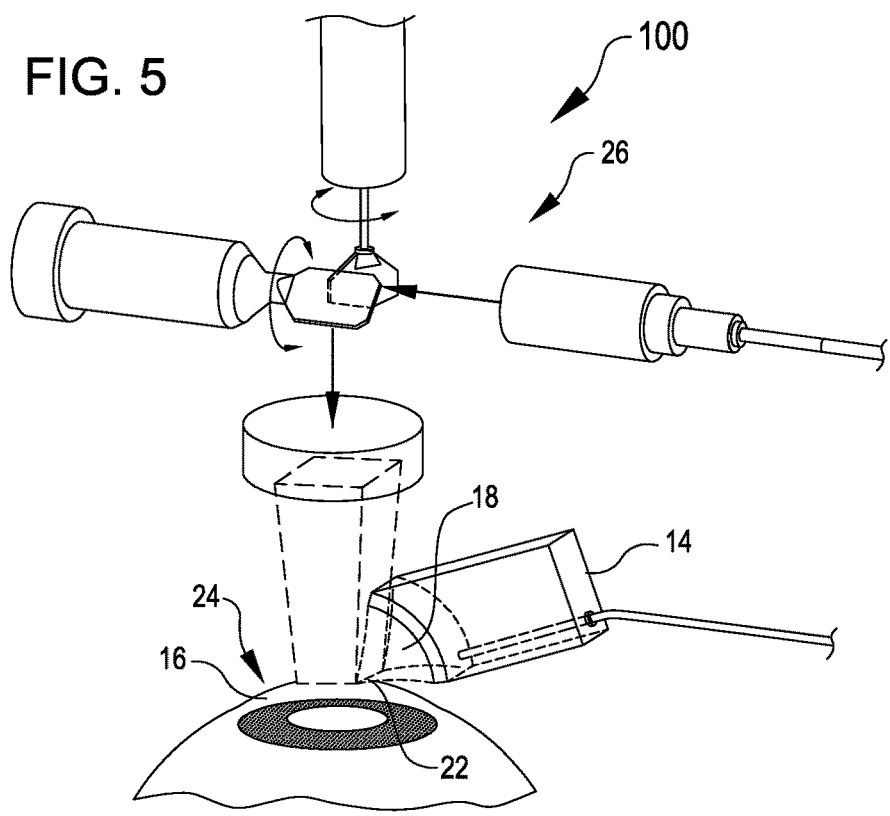
FIG. 5 shows components of a dynamic elastography system for mapping elastic properties of a cornea, in accordance with embodiments.
Figure 6A:
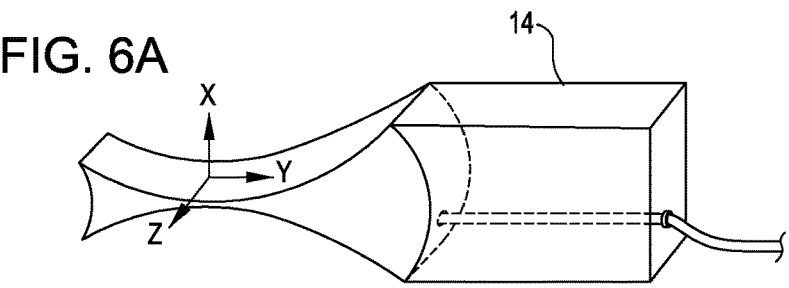
FIGS. 6A, 6B, 6C, and 6D illustrate transmitting ultrasound through air with a focused, air-coupled transducer, in accordance with embodiments.
Figure 6B:
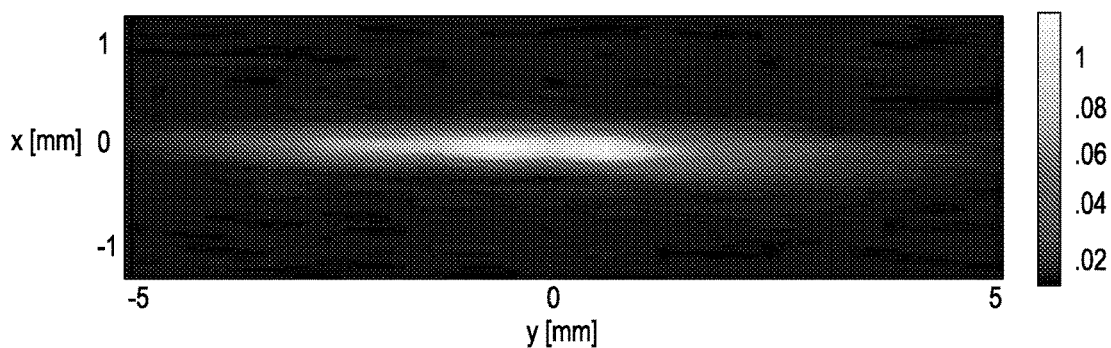
Figure 6C:
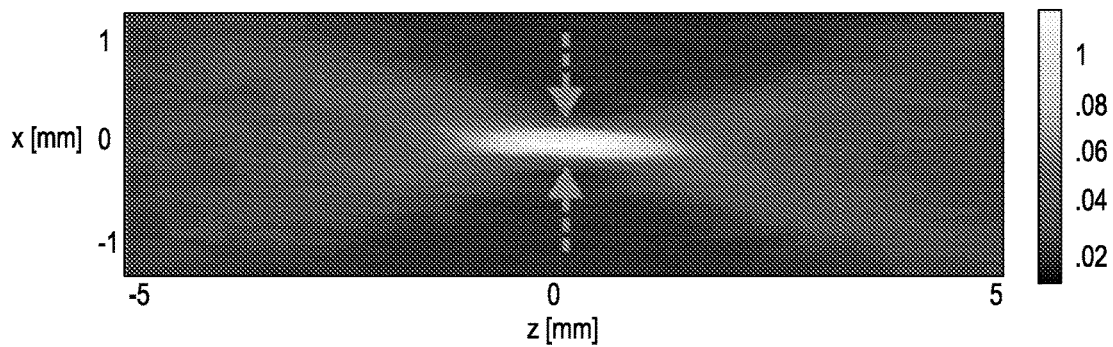
Figure 6D:
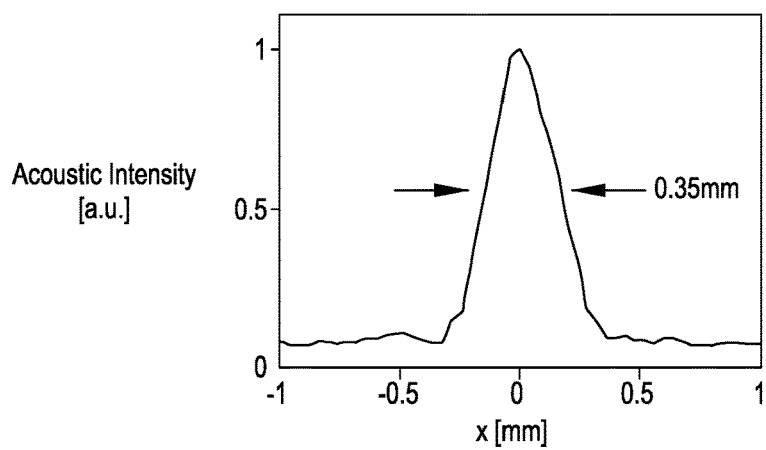

FIG. 5 shows components of a dynamic elastography system 100 for mapping elastic properties of a cornea, in accordance with embodiments. The system 100 includes a focused air-coupled ultrasound transducer 14 and a PhS-OCT imaging system 26. The dynamic elastography system 100 employs fully non-contact soft tissue elastography using AμT to excite a broadband mechanical wave in a cornea (soft material 16) and employs 4D tracking of the transverse propagating displacements within the cornea 16 via the PhS-OCT imaging system 26. In the embodiment illustrated in FIG. 5, the PhS-OCT imaging system 26 has A 15,900 frame rate. The dynamic elastography system 100 utilizes an US beam pulse 18 launched with the focused air-coupled transducer 14. The US beam pulse 18 propagate through air to a region 22 on the air/cornea interface 24. The US beam pulse 18 reflects from the region 22, thereby applying a transient acoustic radiation force (ARF) to the cornea 16 at the region 22. The transient ARF applied to the cornea 16 is a function of the spatial shape and the duration of the US beam pulse 18. The US beam pulse 18 "taps" the cornea 16 at the region 22, thereby inducing transient displacement(s) of the cornea 16 at the region 22. The induced transient displacements(s) generate a propagating shear/guided/interface/Lamb wave in the cornea 16 with the mode of the wave being determined by boundary conditions. The generated wave is referred to herein as a mechanical wave. The PhS-OCT imaging system 26 is configured to track propagation of the mechanical wave 12 in four dimensions (i.e., three space dimensions plus time—4D). With the system 100, only 3 ms is required to fully track propagation in a (XZ) plane, and only 0.3 sec is needed to acquire time-dependent volumetric data (entire 4D data set) over a 6 mm×6 mm lateral field of view.

The dynamic elastography system 100 was demonstrated via use of the system 100 to accomplish 4D imaging of mechanical wave propagation in an ex-vivo porcine eye cornea. The efficient excitation of the mechanical wave 12 in the ex-vivo porcine eye cornea 16 with the focused air-coupled transducer 14 and imaging of the mechanical wave 12 with the PhS-OCT imaging system 26 was used to produce snapshots of transient displacements within the cornea 16 at time points during propagation of the wave 12. It takes about 1 ms for a mechanical wave 12 to propagate 6 mm (linear image size in propagating X direction) in the cornea 16. Because the PhS-OCT system 26 acquires 16 snapshots per ms, the propagation of the wave 12 can be easily measured via the PhS-OCT system 26. Experiments were performed on the cornea 16 from a freshly excised porcine eye at four (10, 20, 30 and 40 mmHg) intraocular pressures (IOP) and four (0°, 45°, 90° and 135°, calculated from X-axis) propagation directions for each IOP resulting in 16 complete 4D image volumes.

FIG. 6A through FIG. 6D illustrate an US intensity field emitted by the transducer 14 of the system 100, as measured with a 0.4 mm needle hydrophone (Part #HNC-0400, Onda, USA) directly in air. The transducer 14 of the system 100 is cylindrical focused and therefore the maximum intensity area is localized into a strip in the (XY) plane (see FIG. 6B). The length of the maximum intensity strip determines the length of the AμT source. The distribution of the US intensity field in the (XZ) plane (see FIG. 6C) determines the actual focal zone; the width of the focal zone in the X direction defines the AμT source width shown in FIG. 6D. When the tissue relaxation time from induced tapping is shorter than the tapping time, the characteristic wavelength of the generated mechanical wave is determined by the width of the AμT source in the direction of mechanical wave propagation. The characteristic wavelength of the wave 12 defines the ultimate in-plane imaging resolution.

Figure 7:
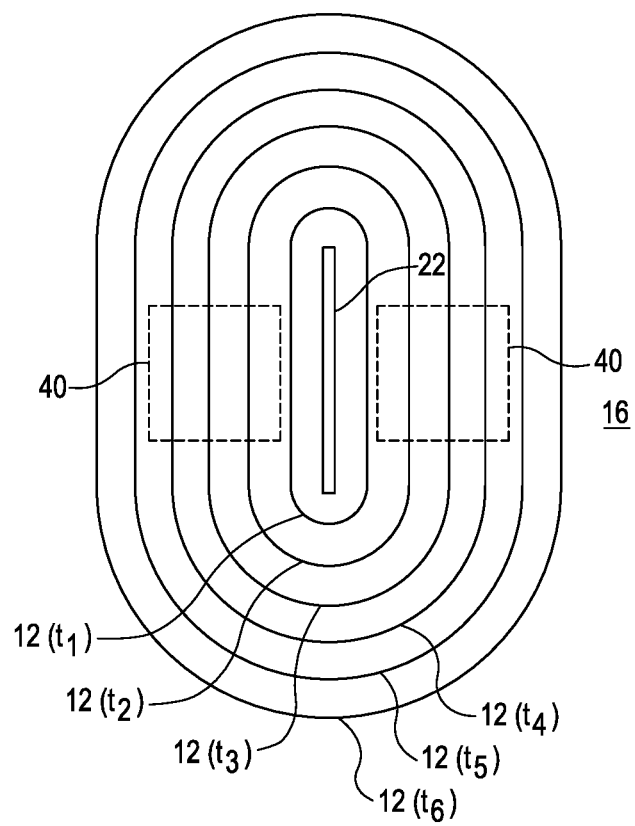
FIG. 7 is a simplified schematic plan-view diagram illustrating an elongated region to which an ultrasound pulse is applied and time sequence images of a resulting mechanical wave generated via the application of the ultrasound pulse, in accordance with embodiments.

FIG. 7 is a simplified schematic plan-view diagram illustrating an elongated region 22 to which an ultrasound pulse is applied and time sequence images (at $t_1$, $t_2$, $t_3$, $t_4$, $t_5$, and $t_6$) of a resulting mechanical wave 12 generated via the application of the ultrasound pulse 18, in accordance with embodiments. Due to the elongated shape of the region 22, there are regions 40 within the soft material 16 adjacent to the region 22 through which the wave 12 propagates in the form of a plane wave or near plane wave, thereby simplifying the determination of elasticity of the soft material within the regions 40. Accordingly, the region 22 can be repositioned and/or reoriented relative to the soft material 16 as suitable to reposition the regions 40 so as to cover desired regions of the soft material 16 with the regions 40 to enable easier determination of elasticity of the soft material 16 over the desired regions of the soft material 16.

Figure 8A:
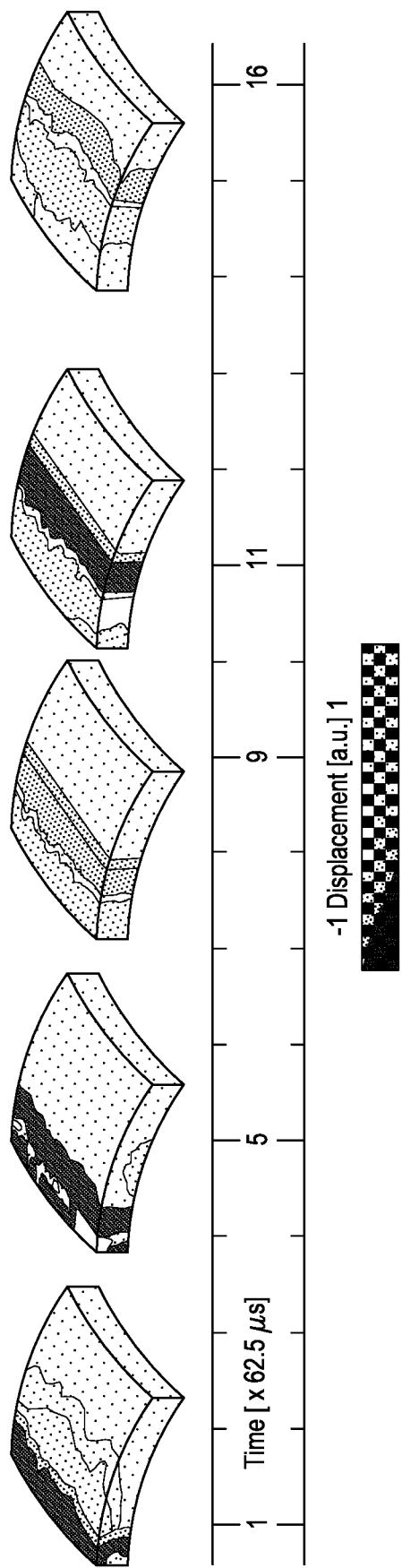
FIGS. 8A and 8B show time sequences of images of propagating waves in ex-vivo porcine eye cornea having different intraocular pressure, in accordance with embodiments.
Figure 8B:
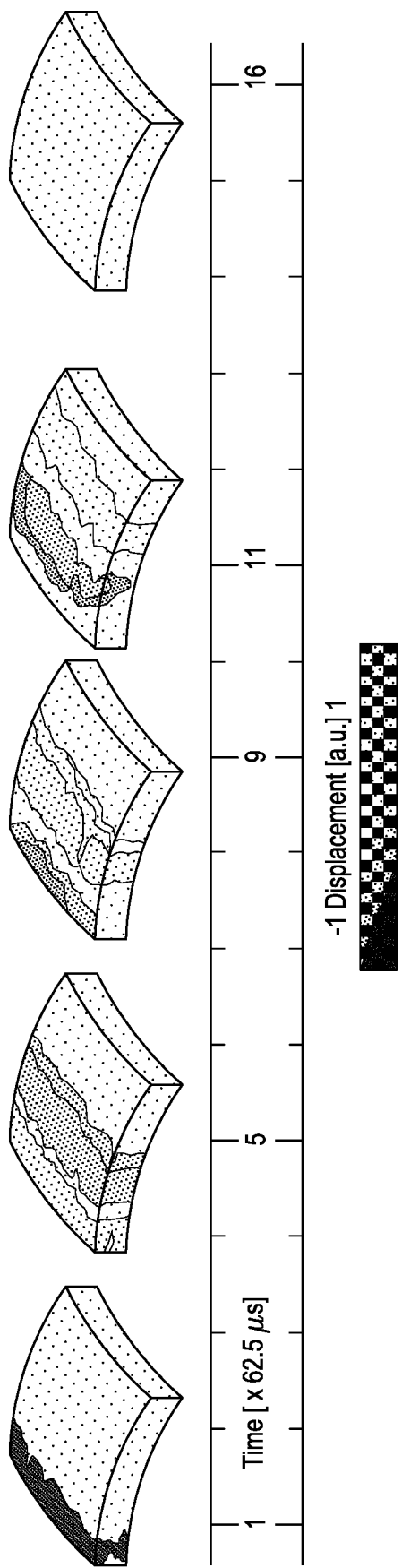

FIG. 8A through FIG. 8B shows two of the 16 4D data sets produced by the dynamic elastography system 100 as described above. The two 4D data sets illustrated include a group of transient displacement snapshots at 10 mmHg IOP (FIG. 8A) and 40 mmHg IOP (FIG. 8B) for 0° propagation, respectively. As expected, AμT with the cylindrically focused transducer 14 provides a "thin strip" AμT source at the surface 24 of the cornea 16. The strip length corresponds very well to the transducer focal zone in the (XY) plane shown in FIG. 6B. The strip width determines the characteristic wavelength of the propagating wave and localizes displacements to about 0.5 mm, which also corresponds well to the transducer focal zone in the (XZ) plane (FIG. 6B and FIG. 6C), taking into account an approximately 45 degree tilt of the transducer 14 with respect to a normal direction to the surface 24 of the cornea 16.

Both the length and width of the AμT source determine the character of the propagation of the wave 12 within the cornea 16. Over a suitable region of interest of the cornea 16 relative to the region 22, the wavefront curvature does not change over the entire propagation distance and, therefore, the propagation of the wave 12 can be interpreted as simple plane-wave propagation over the region of interest. Plane waves do not diffract, so diffraction effects can be ignored for wave speed estimation. The generation of a plane wave over a region of interest simplifies the determination of wave speed as compared to a spherical wave propagating from a point-like source where frequency-dependent diffraction can be significant. Additionally, the propagating wave in the cornea transmits part of its energy to other portions of the eye. The transmission of energy from the wave 12 to other portions of the eye induces strong frequency dispersion as described herein. When frequency dependent diffraction is also present, extracting quantitative information from experimental data can be a challenge. This is especially true if the elastic modulus is estimated from wave velocities.

As evident in FIG. 8A and FIG. 8B, the mechanical wave 12 propagates much faster at 40 mmHg IOP than at 10 mmHg IOP. For instance, the wave 12 already exits the region by the 16th time instant at 40 mmHg IOP (FIG. 8B), but at 10 mmHg (FIG. 8A) the wave 12 is near the middle of the image at the same instant, indicating increased elasticity of the cornea 16 with increased IOP.

Three-dimensional images of displacements of the soft material induced by the wave 12 can be used to estimate the speed of the wave 12 at every point within the volume using known approaches. The resulting wave speed maps can be used to estimate the elastic modulus for the soft material 16 if the relationship between speed and modulus is well defined for the experimental conditions. The group velocity characterizes the rate of maximum amplitude propagation regardless of the wave harmonic content.

Figure 9A:
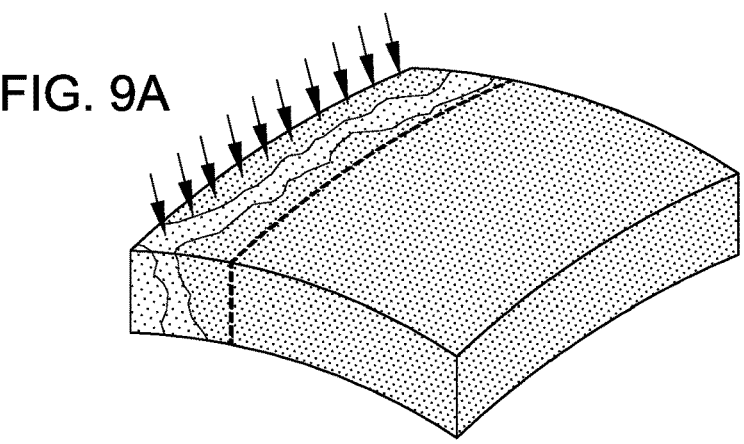
FIGS. 9A and 9B show three-dimensional (3D) distributions of group velocity of a mechanical wave in an ex-vivo porcine eye cornea, in accordance with embodiments.
Figure 9B:
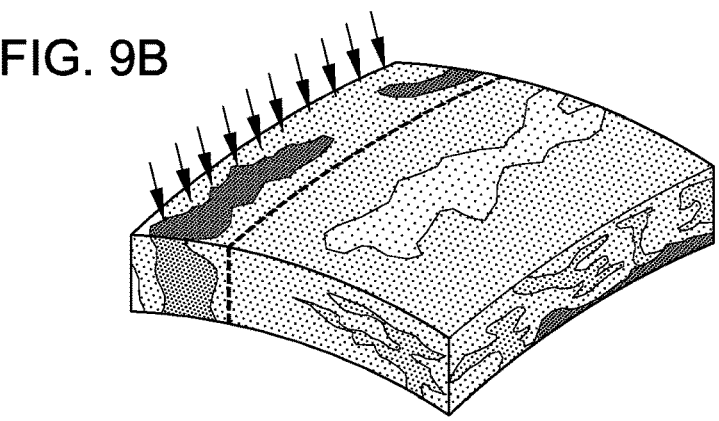
Figure 9C:
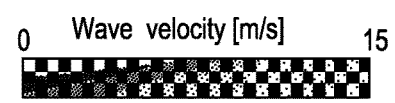
FIG. 9D shows group velocity in an ex-vivo porcine eye cornea for the different positions defined in FIG. 9C and different intraocular pressures, in accordance with embodiments.

FIG. 9A and FIG. 9B present 3D distributions of group velocity in the ex-vivo porcine eye cornea 16. The illustrated 3D distributions of group velocity were computed using a cross-correlation-based phase-zero crossing method. Detected signals separated by 6 (six) spatial points along the trajectory $X_{tr}$, (i.e. $\Delta X_{tr}$=352.8 µm) were cross-correlated to determine the time-lag, $\Delta t_g$, (and, therefore, the group velocity as $V_g=\Delta X_{tr}/\Delta t_g$). The procedure was repeated for all detection points within the volume. Finally, a moving average procedure was applied to the velocity distributions within an effective volume of 294 µm×294 µm×114 µm in X, Y and Z directions, respectively.

Figure 9D:
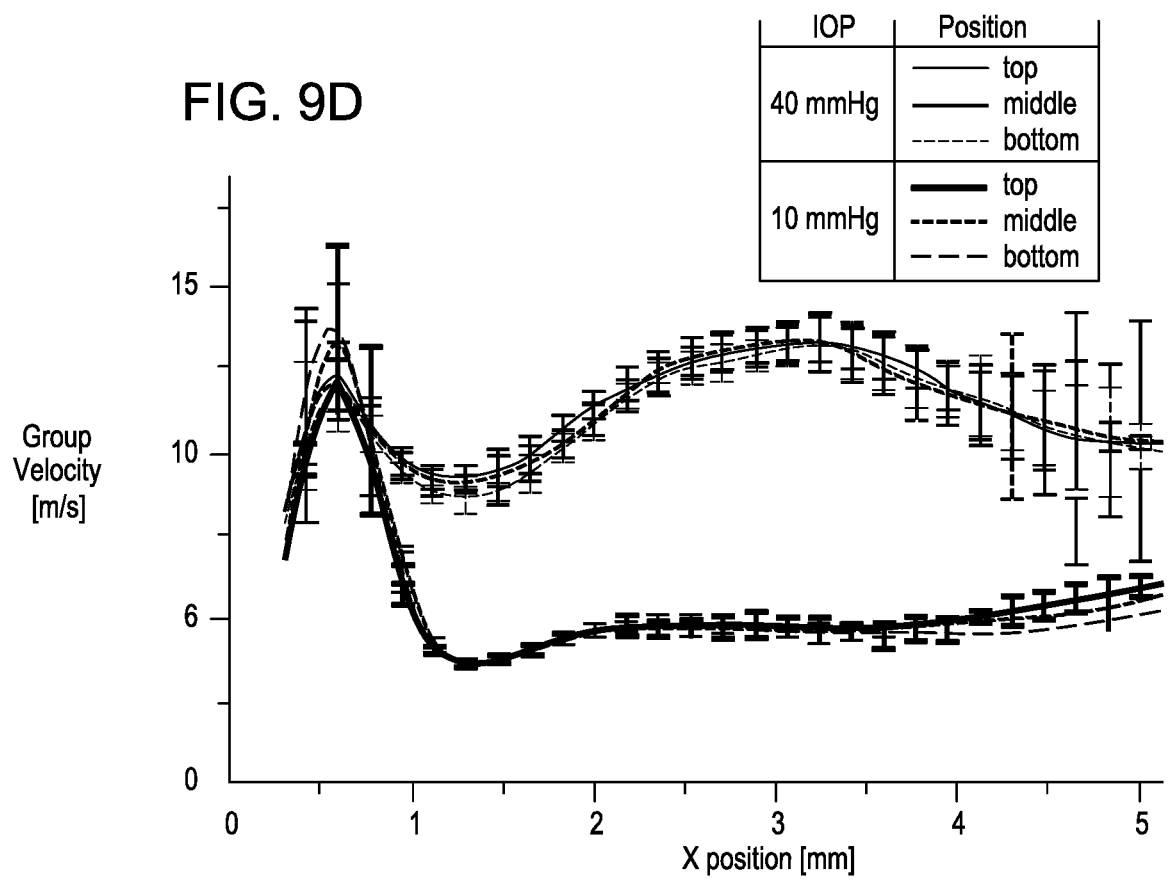

FIG. 9D shows the group velocity versus coordinate $X_{tr}$ for different depths. The group velocity for 10 mmHg IOP at 0° propagation is relatively homogeneous over both propagation distance and depth, except in a near field region (the dashed line in FIG. 9A and FIG. 9B) in which the group speed calculation is incorrect due primarily to artifacts in the OCT signal induced by the ultrasound source. At 40 mmHg IOP and 0° propagation, the group velocity does not change much with depth, but varies with propagation distance. Although a low signal-to-noise ratio for distances larger than 4 mm from the source leads to larger inaccuracies, the group velocity change with distance may be significant. Possibly, the system that was used to maintain the IOP created additional cornea thickness and curvature heterogeneities or non-linear elasticity changes for such an artificially high IOP. Overall, the average group velocity at 40 mmHg IOP is more than twice that at 10 mmHg IOP.

Figure 10:
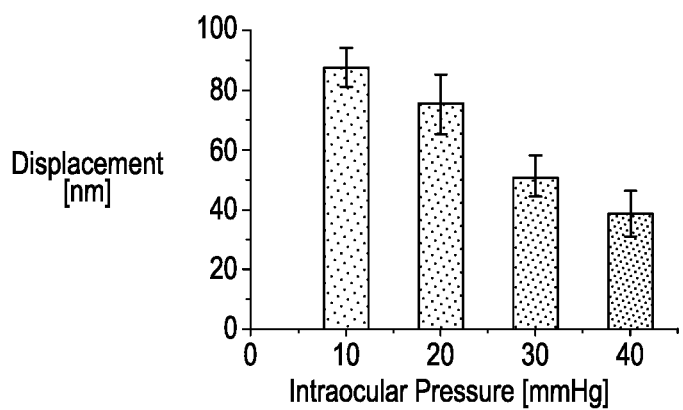
FIG. 10 illustrates reduction in wave amplitude in an ex-vivo porcine eye cornea with increasing intraocular pressure, in accordance with embodiments.

Because the elastic modulus of the cornea 16 can potentially change as a function of IOP and propagation direction, so too can the maximum displacement magnitude near the US source since the US intensity, and, hence, the radiation force is kept constant for all measurements. FIG. 10 shows that the amplitude of the mechanical displacement wave in the cornea 16 averaged within the excitation region decreases with IOP at 0° propagation, consistent with previous US-based acoustic radiation force impulse (ARFI) imaging studies in many tissues showing a strong correlation between higher wave speeds and smaller displacements. Combining quantitative maps of the Young's modulus determined from wave speed measurements, as discussed herein, with simultaneous maps of corneal displacement for a known radiation force and corneal thickness can be used to estimate IOP without any assumptions about cornea mechanical properties. In contrast, current clinical IOP measurement devices assume some average elastic properties for the cornea.

As described herein, reflection-based ARF from air can be used to excite a mechanical transverse wave in porcine eye cornea with sufficient displacement amplitude to be tracked with an imaging system even at very low acoustic pressures. The acoustic intensity employed is many times smaller than safety guidelines used in diagnostic ultrasound. Because both US and OCT are already used extensively in the clinic, there appears to be a straightforward path to translate the systems and methods described herein (e.g., AµT-OCE) into a routine clinical tool.

The approaches for dynamic elastography using AµT described herein can be used to generate more accurate estimation of IOP than current air-puff/tonometry-based methods. Cornea elasticity is strongly dependent on IOP. Collagen fibers within soft tissues such as the cornea tend to bear primary mechanical loads. Crimped collagen fibers gradually elongate and interact with the hydrated tissue matrix. This creates a strong non-linearity in the stress-strain relation, i.e., elastic moduli (including elasticity) depend on applied stress.

As described herein, not only have applicants demonstrated efficient AµT-based imaging of a mechanical wave in biological tissue, but also that the wave propagation speed and displacement amplitude can be measured at each point of the imaged volume. By processing the observed wave speeds within the imaged volume, quantitative estimates of elastic (Young's) modulus can be made throughout the imaged volume using known techniques. A combination of the modulus, the size and shape of the cornea, and displacement maps can be used with an appropriate biomechanical model to image not only the elastic properties but also estimate the IOP independent of cornea mechanical properties. Because the mode type of the generated mechanical wave 12 greatly influences how wave speed measurements are converted into modulus estimates, the appropriate mode can be identified for each application. For the porcine cornea results presented here, the primary mode is a guided (Lamb) wave with significant frequency dispersion over the kHz range given the thickness of the cornea relative to a shear wave wavelength. Consequently, dispersion can be taken into account to produce quantitative measures of the Young's modulus.

Figure 11A:
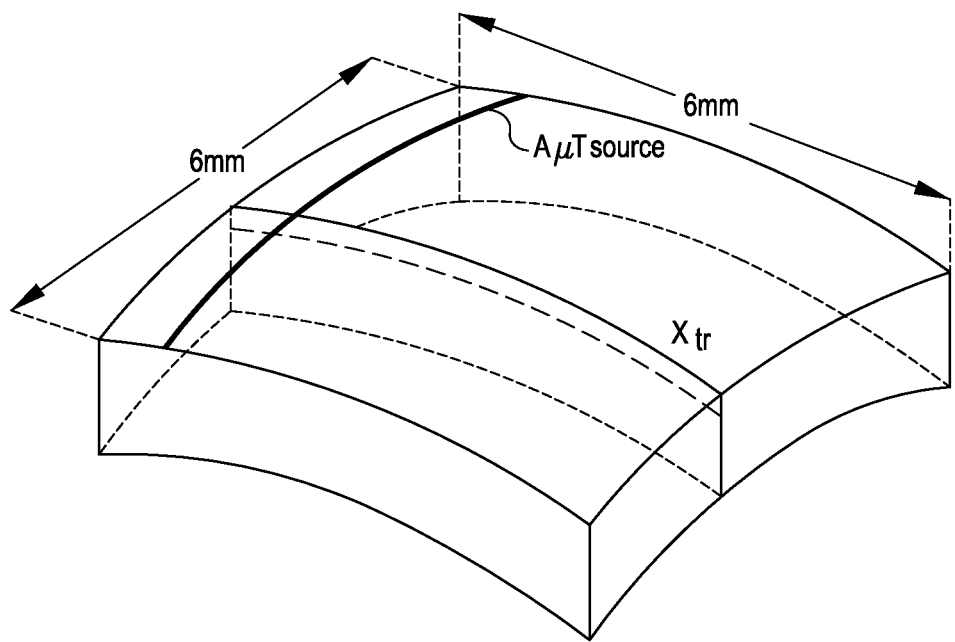
FIGS. 11A, 11B, 11C, 11D, and 11E illustrate the impact of dispersion and intraocular pressure on the propagation of a mechanical wave in an ex-vivo porcine eye cornea, in accordance with embodiments.
Figure 11B:
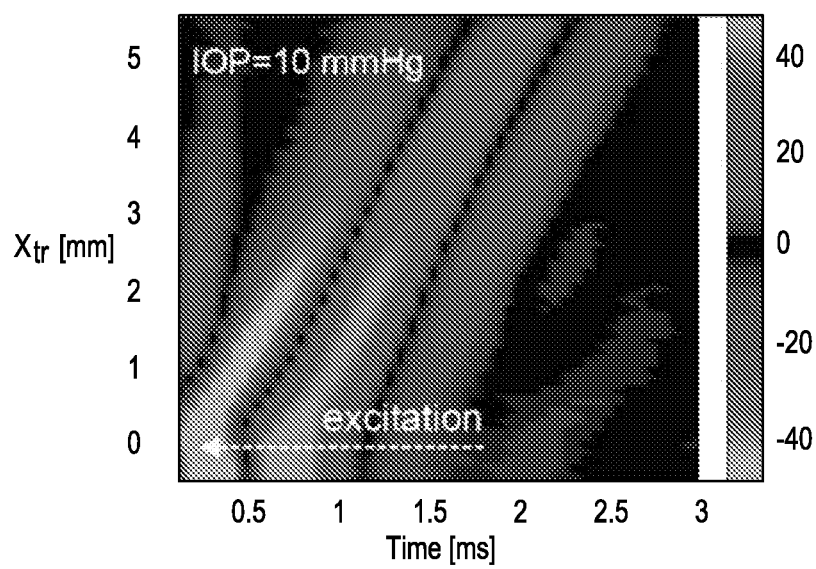
Figure 11C:
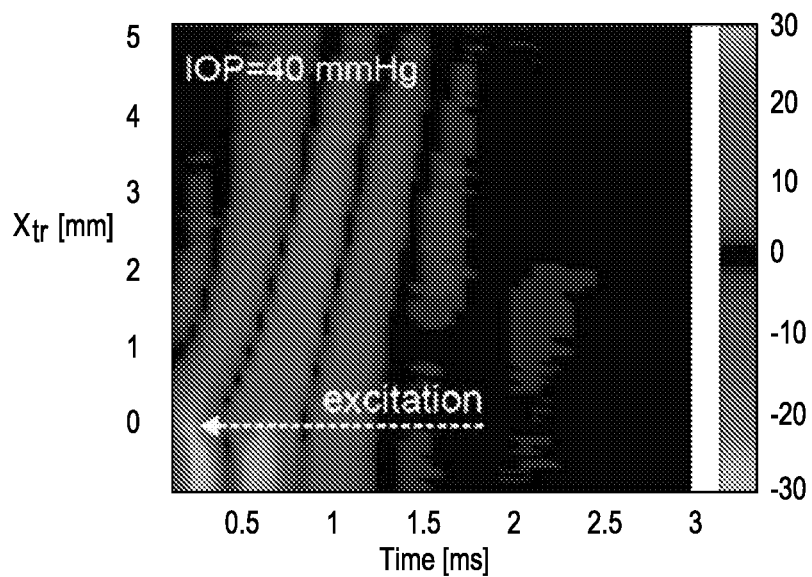

To illustrate the role of dispersion in OCE of the cornea, consider a particular propagation trajectory (dashed line in FIG. 11A) and the transient displacement as a function of propagation distance, $X_{tr}$, and time along this path, as shown in FIG. 11B and FIG. 11C at 10 mmHg and 40 mmHg IOP for 0° propagation, respectively. The local slope of the $X_{tr}$-t plots determines the group velocity of the propagating wave. As shown, the group velocity is over two times larger at 40 mmHg IOP than at 10 mmHg IOP.

Figure 11D:
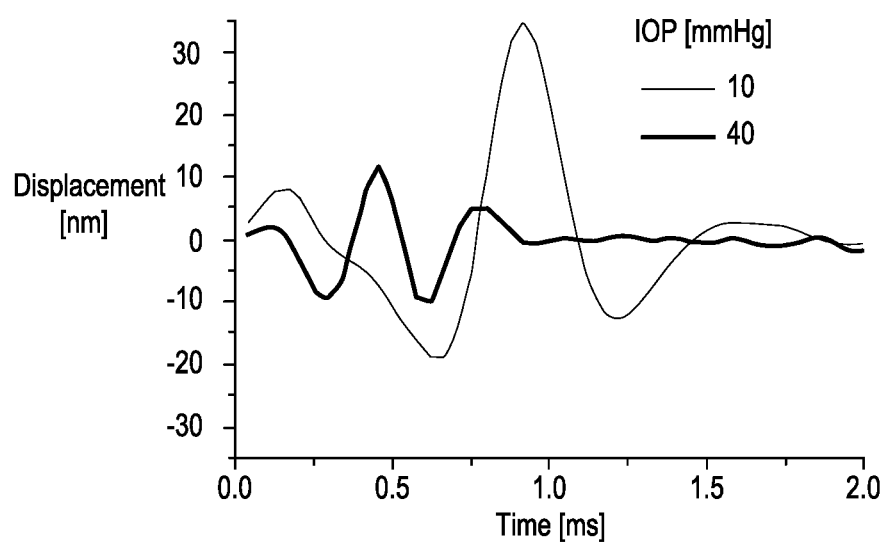
Figure 11E:
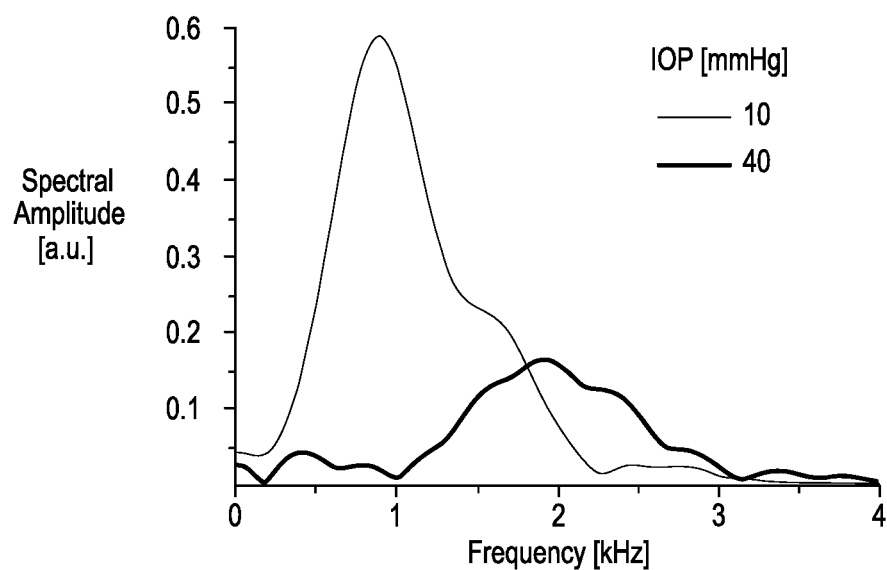

Additional information can be extracted from the imaged wave propagation. For example, the temporal profile of the displacement at a fixed $X_{tr}$ position (FIG. 11D) is much wider at 10 mmHg IOP than at 40 mmHg. The difference in temporal profile of the displacement at a fixed $X_{tr}$ position is also quite clear in the frequency domain (FIG. 11E), where the center frequency of the signal spectrum shifts significantly (~1 kHz for 10 mmHg versus ~2 kHz for 40 mmHg). Thus, the higher the IOP, the larger the characteristic frequency of the mechanical wave excited for the same AµT source. Like the wave speed and displacement magnitude, the characteristic frequency is related to both the elastic modulus and the IOP.

Figure 12:
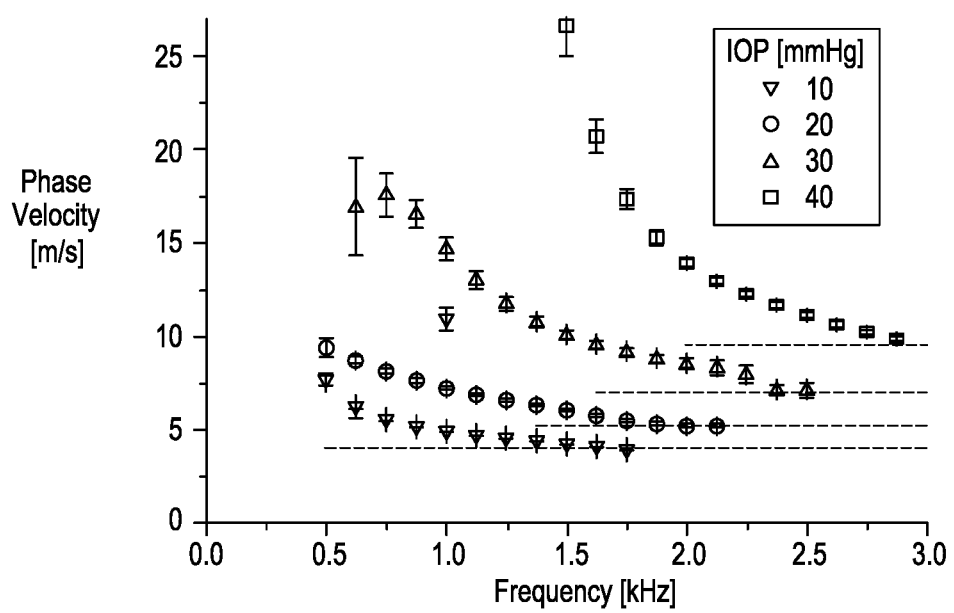
FIG. 12 shows a typical phase velocity frequency dispersion curves obtained for the trajectory illustrated in FIG. 11A, different intraocular pressures, and averaged for a region of Xtr between 2 and 3 mm from the focal region, in accordance with embodiments.

The displacement time waveforms can also be used to estimate the phase velocity, i.e., the phase increment with time, as a function of signal frequency given the broadband character of the propagating wave. FIG. 12 shows typical phase velocity frequency dispersion curves obtained for the trajectory illustrated in FIG. 11A and averaged for a region of $X_{tr}$ between 2 and 3 mm from the AµT source. The same trajectory was used for all IOP over the range of 10-40 mmHg for 0° propagation.

The dispersion is clearly very strong, especially for high IOP. The dispersion is determined mostly by boundary conditions and the thickness of the layer. For the cornea, the mechanical wave in this frequency range is localized primarily within the cornea but leaks inside the eye interior during propagation. Unlike wave propagation in unbounded media where only two propagating modes are present (i.e. longitudinal and shear for an isotropic case), wave propagation in bounded materials supports multiple Lamb modes determined by the frequency range and wave excitation conditions. Because only the displacement along the optical beam path is recorded with OCT, mode polarization is also important. A key parameter is the ratio of the layer (cornea) thickness to wavelength of the propagating wave. In the present case, the ratio of the layer (cornea) thickness to wavelength of the propagating wave is about 2 and four lower-order modes can exist simultaneously. Thus, the dispersion curves illustrated in FIG. 12 may contain a few modes.

A detailed analysis of mechanical mode propagation in a bounded medium is complicated, which requires a careful theoretical analysis accounting for the eye spherical geometry. There are, however, a few important points described below regarding the curves illustrated in FIG. 12 that indicate that quantitative modulus maps for a cornea may be obtained with AµT-OCE.

First, using only the group velocity for cornea elasticity assessment may produce inaccurate results and may lead to erroneous conclusions, especially if low bandwidth signals are considered. The group velocity strongly depends on the frequency range or characteristic wavelength. For example, at 1 kHz the group velocity can be twice that at 2 kHz for the primary mode excited here, directly leading to a fourfold difference in estimates of tissue elasticity. Group velocity based methods using different carrier frequencies and bandwidths will result in different elasticity estimates of the same bounded material.

Full dispersion analysis with broadband waves produced by AµT can overcome these limitations. To properly compute the elastic modulus for a bounded medium, the bulk shear (not guided) wave speed can be used. The speed of the bulk shear wave is uniquely related to the high frequency limit (dashed lines in FIG. 12), determined by either the speed of the Rayleigh wave (for zero order modes) or the speed of bulk shear wave (for higher order Lamb modes). Thus, the high frequency limit of the phase velocity can be used instead of the group velocity to produce quantitative estimates of the shear/Young's modulus in ARF-based elasticity imaging of bounded media such as the cornea. The modulus estimated in this way does not depend on the bandwidth of mechanical waves and is appropriate for biomechanical predictions of near-static deformations in the cornea.

The elastic modulus in the cornea may be anisotropic. Whether the elastic modulus in the cornea is anisotropic or near isotropic may be related with cornea thickness fluctuation. The AµT approach described herein can be used to measure anisotropy with multiple samples used for correct statistics. In the demonstration described herein, no significant anisotropy (>5%) in the elastic modulus of the porcine cornea was observed for all IOP in the range of 10-30 mmHg and all (0°, 45°, 90° and 135°) propagation directions. For 40 mmHg IOP, increased wave velocity of ~25% for 135° propagation was observed, but could be related with true anisotropy or a non-linear change of cornea elasticity for such high IOP.

The AµT-OCE imaging system employed in the demonstration described herein is a simple proof-of-concept device that can be greatly improved for clinical applications. For example, the air-coupled ultrasound transducer employed contains a single element providing a single cylindrical focus to one position. To induce a mechanical wave at a different position, the transducer employed must be physically moved. The AµT-OCE imaging system employed can be replaced with an array of US elements, similar to conventional medical US arrays operating in the low MHz regime. The AµT source can be moved electronically and multiple foci synthesized simultaneously using array processing. Recent work in US shear wave imaging has shown that multiple simultaneous source positions distributed laterally combined with directional filtering of displacement waveforms can greatly increase the size of the tissue volume probed with a single mechanical excitation.

The AµT-OCE imaging system employed in the demonstration described herein can be modified to employ an improved imaging system relative to the PhS-OCT imaging system described herein. In the AµT-OCE imaging system employed in the demonstration described herein, the OCE lateral field of view is limited to 6 mm×6 mm, which is not sufficient to cover the entire cornea. To improve the field of view, both the OCT scanning system and AµT source can be scanned. Additionally, in the AµT-OCE imaging system employed in the demonstration described herein, 10 signal averages (10 repeated B-scans) are used to achieve sufficient signal-to-noise ratio (SNR) for imaging and characterization of propagating mechanical waves in the cornea, which increases the time needed for data acquisition.

In addition, the imaging system used can employ an OCT system that incorporates recent advances in laser technology to greatly increase the 3-D scan rate. The latest generation of swept source lasers providing A-Scan rates over 20 MHz, with multi-beam configuration, can potentially increase scan rates by a factor of ten. By reducing the number of signal averages employed, combined with higher scan rates, the full 3-D volume of the cornea may be able to be imaged in less than 1 sec. Combining an air-coupled array approach with faster OCT scan rates may enable real-time, or near real-time, OCE of a cornea.

Quantitative elastic modulus maps offer exciting opportunities to better understand and evaluate corneal biomechanics in diseases (such as keratoconus) and in surgical planning (refractive surgery and corneal transplant surgeries). Furthermore, AµT-OCE can provide new insights into the role of elasticity in many ophthalmic conditions such as ocular surface tumor characterization, scleral elasticity and myopia, and risk factors in glaucoma progression. Also, AμT-OCE can be used to study changes in corneal elasticity induced by interventions such as laser surgery.

AμT-OCE is not limited to the cornea. AμT-OCE can be easily adapted for use in many medical applications where optical methods are currently used, such as characterization of skin elasticity or mapping the elastic properties of tissue biopsies. AμT-OCE may be suitable for clinical use because it is absolutely non-contact and can provide real time results. AμT-OCE as described herein is believed by applicants to be the first experimental demonstration of non-contact ARF-based generation of a broad bandwidth mechanical wave in soft tissues; and the first experimental demonstration of a fully non-contact and non-invasive method for soft media elasticity characterization combining air-coupled ultrasound and PhS-OCT.

While the AμT approaches described herein may be particularly suitable for application to biological tissue, many non-medical uses are also possible. For example, the elasticity of any soft material, especially fragile materials, can be characterized because no contact is made with the sample. In most cases, the acoustic impedance of a soft material is much different than that of air, so AμT can efficiently launch a transverse mechanical wave in the soft material without contact. A number of imaging approaches can potentially monitor mechanical wave propagation to assess the elastic properties of the soft material. In this way, AμT can become a routine tool to assess the elastic properties of soft materials, especially delicate samples easily damaged by contact or soft materials where contact may change the elastic properties of the soft material.

Methods

The porcine eye used in the demonstration of the AμT-OCE as described herein was enucleated immediately after death. The OCE measurements were performed within 20 hours after enucleating. Before performing any measurements, the porcine eye was kept in a refrigerator at 4° C. within a chamber, surrounded by cotton soaked in physiological saline. During measurement, the whole porcine eyeball was placed into a custom-built holder with a half-sphere cup and moisturized cotton to provide an in situ environment. The eye globe was oriented with cornea side up and the optic axis vertical. The OCE scanning beam paralleled the optic axis. A 23 G needle was inserted through the sclera of the porcine eye and connected to an infusion reservoir at the other end. The IOP within the procine eye was controlled by adjusting the height of an infusion reservoir.

Figure 13:
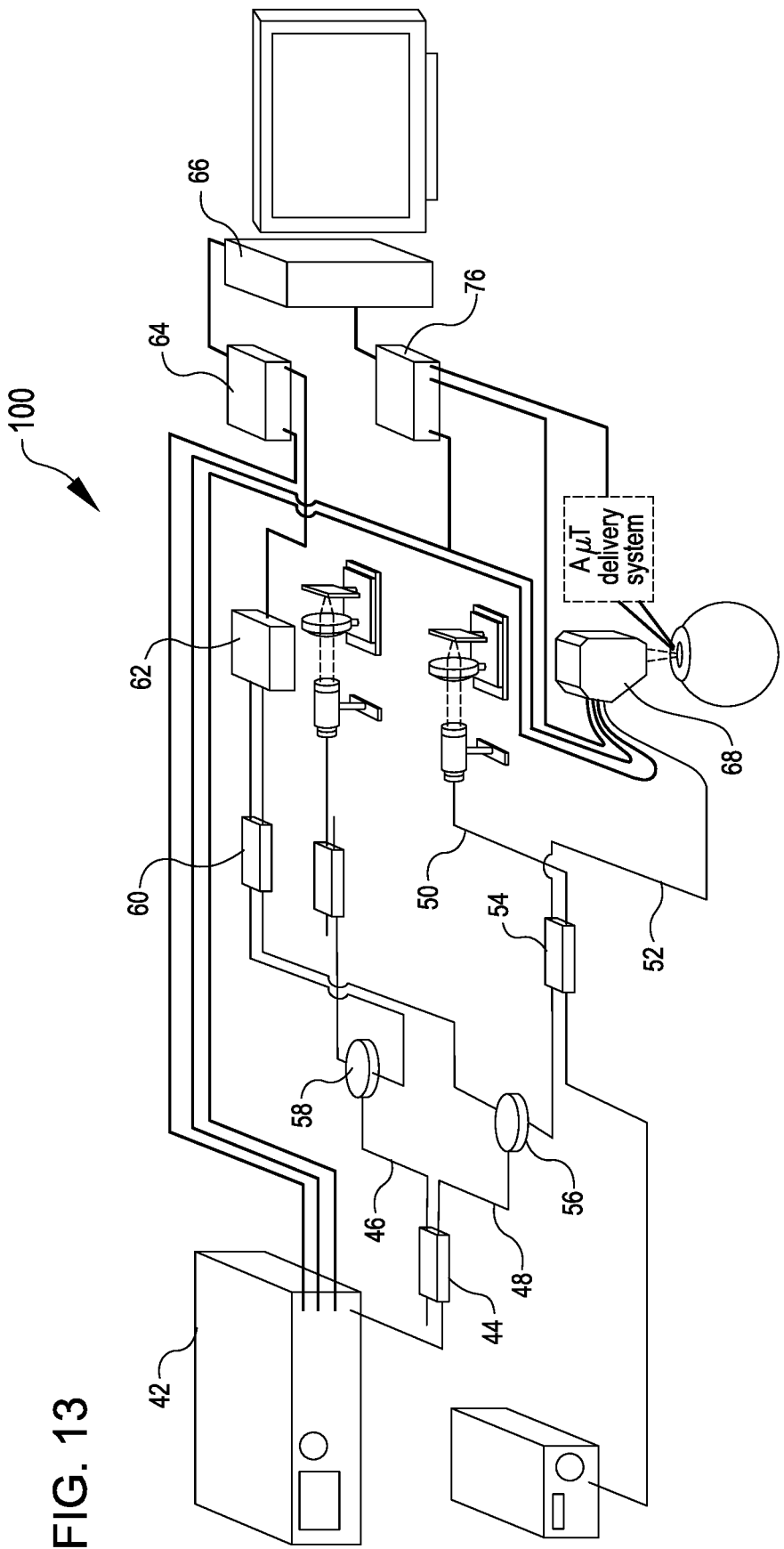
FIG. 13 illustrates a dynamic elastography system for mapping elastic properties of a cornea, in accordance with embodiments.

To track the tissue displacement in 4D with high sensitivity and high resolution, a fast PhS-OCT system 26 was developed (FIG. 13). A commercially available high-speed FDML swept laser 42 (Optores GmbH, Germany) was employed as the OCT light source capable of 1.62 MHz sweep repetition rate over a spectral bandwidth of 110 nm centered at 1308 nm. The output light from the laser 42 is coupled into the PhS-OCT system 26 via a 90/10 fiber coupler 44 with 10% of light routed to the reference arm 46. The rest of the output light from the laser 42 is routed to the sample arm 48, where it is further split into a calibration arm 50 and the sample arm 52 via a 99/1 fiber coupler 54. The calibration arm 50 combined with the reference arm 46 formed a slave interferometer providing a reference signal to quickly calibrate spectral interferograms for OCT signal reconstruction. Back-scattered light from the sample arm 52 and light from the reference arm 46 each pass through an optical circulator 56, 58 and are then combined by a 50/50 fiber coupler 60, forming a Mach-Zehnder interferometer that generates the OCT signal. The OCT signal is detected by a high-speed balanced photo detector 62 (PDB480C-AC, Thorlabs Inc., USA), and subsequently digitized by an analog to digital converter card 64 (ATS9373, AlazarTech, Canada) at 3.6 GS/s. Captured data are transferred to a host PC 66 through PCIe bus, and finally processed for real-time preview, or stored for later processing.

An OCT probe 68 (see FIG. 5) in the sample arm 48 contains a dual-axis galvanometer scanner 70 and an object lens 72 with a 35 mm focal length. The dual-axis scanner 70 is resonant (Electro-Optical Products Corp., USA). The dual-axis scanner 70 is driven by a triangle waveform (7950 Hz) and synchronized by a phase lock loop (PLL) module on the FDML laser 42.

Both directions of the scanned, focused sample beam were used to produce B-Scans at a rate of 15,900 frames per second. For each B-scan, there were 102 A-scans. These parameters parallel those described in previous studies of phase-stabilization strategies. The slow axis of the dual-axis scanner 70 is driven by a galvo motor 74 (6215H, Cambridge Technology, USA) to sweep a full volume of B-Scans. The axial (in-depth) resolution of the PhS-OCT system 26 was measured to be ~15 μm in air. The lateral resolution of the PhS-OCT system 26 is 58.8 μm over the entire scan area (lateral field of view) of 6 mm×6 mm. The system ranging distance was up to 4 mm.

The scan protocol and synchronization of AμT was controlled by an analog output device 76 (PCI6713, National Instruments, USA). For each AμT excitation, the 4-D scanning protocol repeated 48 B-scans separated by 62.5 μs to collect a time course of B-scans, i.e., full M-B scan taking just 3 ms. There were 102 AμT excitations, each synchronized with the first B-scan on each image plane, resulting in 102 image planes to cover the entire 3-D region of interest in only 0.3 sec. The procedure was repeated 10 times to improve the signal-to-noise ratio, resulting in a total data acquisition time of 3 sec.

The displacement within the cornea was computed from the phase of the OCT signal, as described herein. For each volume, the displacement field was extracted to measure wave propagation. Distortion from non-linear resonant scanning was corrected by spatial re-sampling, and sample time differences between beams within one B-scan were corrected by temporal re-sampling. Potential surface ripple artifacts were also suppressed using an automatic surface detection method described in a previous study.

FIG. 14 is a simplified schematic diagram of acts of a method 200 of measuring one or more properties of a soft material using air-transmitted ultrasound to generate mechanical waves in the soft material, in accordance with embodiments. Any suitable system, including the AμT systems (e.g., non-contact AμT-OCE) described herein, can be used to practice acts of the method 200. The method 200 includes transmitting ultrasound through air to a focal region on an interface boundary between a soft material and air (act 202), applying a force on the focal region by reflecting the ultrasound from the focal region (act 204), generating mechanical waves in the soft material as a result of the force applied at the focal region (act 206), measuring propagation of the mechanical waves in the soft material with an imaging system (act 108), and determining the one or more properties of the soft material based on the measured propagation of the mechanical waves in the soft material (act 210).

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of measuring one or more properties of a soft material, the method comprising:
    transmitting ultrasound through air to a region on an interface boundary between the soft material and air;
    applying a force on the region by reflecting the ultrasound from the region;
    generating a mechanical wave in the soft material as a result of the force applied at the region;
    measuring propagation of the mechanical wave in the soft material with an imaging system; and
    determining the one or more properties of the soft material based on the measured propagation of the mechanical wave in the soft material.

2. The method of claim 1, wherein the region has an elongated shape having a length and a width, the length being at least ten times the width.

3. The method of claim 1, wherein:
    transmitting the ultrasound through air to the region comprises focusing the ultrasound onto the region using at least one of a focused ultrasonic transducer, an acoustic lens, an acoustic mask, a focusing mirror, and a Fresnel plate;
    transmitting the ultrasound through air to the region comprises transmitting the ultrasound by an array of ultrasonic transducers; and
    transmitting the ultrasound through air to the region comprises transmitting the ultrasound by an ultrasound transducer coupled to the air.

4. The method of claim 1, wherein measuring the propagation of the mechanical wave in the soft material with the imaging system comprises generating a time sequence of images of the mechanical wave.

5. The method of claim 4, wherein the imaging system comprises at least one of an optical imaging system, an ultrasound imaging system, and magnetic resonance imaging ("MRI") system.

6. The method of claim 4, wherein determining the one or more properties of the soft material based on the measured propagation of the mechanical wave in the soft material comprises generating a spatial map of elastic modulus of the soft material for locations in the soft material based on measured displacements of the locations in the soft material in the time sequence of images.

7. The method of claim 5, wherein the imaging system includes an optical coherence tomography ("OCT") system.

8. The method of claim 7, wherein the OCT system includes a phase-sensitive OCT system.

9. The method of claim 8, wherein a phase of the OCT signal at a pixel in an image of the time sequence of images is used to detect displacement of a location in the soft material corresponding to the pixel.

10. The method of claim 8, wherein the time sequence of images comprises both two-dimensional and three-dimensional OCT images that are used to measure displacements at locations in the soft material induced by the mechanical wave.

11. The method of claim 1, wherein the soft material is one of a cornea, skin, a biopsy sample, and a gel-based material.

12. The method of claim 1, wherein:
    the soft material comprises an eye having a cornea;
    the region is on an interface boundary between the cornea and air;
    the mechanical wave is generated in the cornea; and
    the one or more properties of the soft material comprises an intraocular pressure of the eye.

13. A system for measuring one or more properties of a soft material, the system comprising:
    an ultrasound transducer assembly operable to transmit ultrasound through air to a region on an interface boundary between the soft material and the air, wherein the ultrasound applies a force on the region by reflecting from the region, and wherein the application of the force to the region generates a mechanical wave in the soft material;
    an imaging system configured to generate image data of propagation of the mechanical wave in the soft material;
    a processor; and a tangible memory device storing non-transitory instructions executable by the processor to cause the processor to process the image data generated by the imaging system to determine one or more properties of the soft material.

14. The system of claim 13, wherein the region has an elongated shape with a length and a width, the length being at least ten times the width.

15. The system of claim 13, wherein:
the ultrasound transducer assembly comprises at least one of a focused ultrasonic transducer, an acoustic lens, an acoustic mask, a focusing mirror, and a Fresnel plate;
the ultrasound transducer assembly comprises an array of ultrasonic transducers; and
the ultrasound transducer assembly comprises an ultrasound transducer coupled to air.

16. The system of claim 13, wherein the image data generated by the imaging system comprises a time sequence of images of the mechanical wave.

17. The system of claim 16, wherein the imaging system comprises at least one of an optical imaging system, an ultrasound imaging system, and magnetic resonance imaging ("MRI") system.

18. The system of claim 16, wherein the tangible memory device stores non-transitory instructions executable by the processor to cause the processor to generate a spatial map of elastic modulus of the soft material for locations in the soft material based on measured displacements of the locations in the soft material in the time sequence of images.

19. The system of claim 16, wherein the imaging system is an optical coherence tomography ("OCT") system.

20. The system of claim 19, wherein the OCT system is a phase-sensitive OCT system.

21. The system of claim 20, wherein a phase of the OCT signal at a pixel in an image of the time sequence of images is used to detect displacement of a location in the soft material corresponding to the pixel.

22. The system of claim 16, wherein the time sequence of images comprises both two-dimensional and three-dimensional OCT images that are used to measure displacements at locations in the soft material induced by the mechanical wave.

23. The system of claim 13, wherein the soft material is one of a cornea, skin, a biopsy sample, and a gel-based material.

24. The system of claim 13, wherein:
the soft material comprises an eye having a cornea;
the region is on an interface boundary between the cornea and air;
the mechanical wave is generated in the cornea; and
the one or more properties of the soft material comprises an intraocular pressure of the eye.

* * * * *